(12) United States Patent
Hashimshony et al.

(10) Patent No.: US 7,904,145 B2
(45) Date of Patent: Mar. 8, 2011

(54) CLEAN MARGIN ASSESSMENT TOOL

(75) Inventors: Dan Hashimshony, Givat Ada (IL); Gil Cohen, Jerusalem (IL); Iddo Geltner, Herzlia (IL)

(73) Assignee: Dune Medical Devices Ltd., Caesarea (IL)

( * ) Notice: Subject to any disclaimer, the term of this patent is extended or adjusted under 35 U.S.C. 154(b) by 0 days.

(21) Appl. No.: 11/745,334

(22) Filed: May 7, 2007

(65) Prior Publication Data

US 2008/0039742 A1 Feb. 14, 2008

Related U.S. Application Data

(63) Continuation-in-part of application No. 11/743,028, filed on May 1, 2007, which is a continuation-in-part of application No. 10/558,831, filed as application No. PCT/IL2005/000330 on Mar. 23, 2005, now Pat. No. 7,720,532.

(60) Provisional application No. 60/555,901, filed on Mar. 23, 2004.

(51) Int. Cl.
*A61B 5/05* (2006.01)
*A61B 5/04* (2006.01)

(52) U.S. Cl. .......... 600/547; 607/901; 600/372; 600/373

(58) Field of Classification Search ................. 324/632, 324/643; 600/372, 373, 382, 439, 547, 587; 607/901
See application file for complete search history.

(56) References Cited

U.S. PATENT DOCUMENTS 3,830,224 A 8/1974 Vanzetti et al.
(Continued)

FOREIGN PATENT DOCUMENTS

AU 688 352 B2 3/1998
(Continued)

OTHER PUBLICATIONS

U.S. Appl. No. 60/641,081, filed Jan. 4, 2005, D. Hashimshony.
(Continued)

*Primary Examiner* — Max Hindenburg
*Assistant Examiner* — Adam J Eiseman
(74) *Attorney, Agent, or Firm* — Browdy and Neimark, PLLC

(57) ABSTRACT

An integrated tool is provided, having a tissue-type sensor, for determining the tissue type at a near zone volume of a tissue surface, and a distance-measuring sensor, for determining the distance to an interface with another tissue type, for (i) confirming an existence of a clean margin of healthy tissue around a malignant tumor, which is being removed, and (ii) determining the depth of the clean margin. The integrated tool may further include a position tracking device and an incision instrument. The soft tissue may be held within a fixed frame, while the tumor is being removed. Additionally a method for malignant tumor removal is provided, comprising, fixing the soft tissue within a frame, performing imaging with the handheld, integrated tool, from a plurality of locations and orientations around the soft tissue, reconstructing a three-dimensional image of the soft tissue and the tumor within, defining a desired clean margin on the reconstructed image, calculating a recommended incision path, displaying the recommended path on the reconstructed image, and cutting the tissue while determining its type, at the near zone volume of the incision surface. The method may further include continuously imaging with the cutting, continuously correcting the reconstructed image and the recommended incision path, and continuously determining the tissue type, at the near zone volume of the incision surface.

28 Claims, 24 Drawing Sheets

U.S. PATENT DOCUMENTS

| | | | |
|---|---|---|---|
| 4,291,708 A | 9/1981 | Frei et al. | |
| 4,344,440 A | 8/1982 | Aaby et al. | |
| 4,458,694 A | 7/1984 | Sollish et al. | |
| 4,537,203 A | 8/1985 | Machida | |
| 4,539,640 A | 9/1985 | Fry et al. | |
| RE32,000 E | 10/1985 | Sagi | |
| 4,617,939 A | 10/1986 | Brown et al. | |
| 4,625,171 A | 11/1986 | Sekihara et al. | |
| 4,682,594 A | 7/1987 | Mok | |
| 4,689,567 A | 8/1987 | Maudsley | |
| 4,751,464 A | 6/1988 | Bridges | |
| 4,768,513 A | 9/1988 | Suzuki | |
| 4,785,806 A | 11/1988 | Deckelbaum | |
| 5,115,137 A | 5/1992 | Andersson-Engels et al. | |
| 5,143,079 A | 9/1992 | Frei et al. | |
| 5,227,730 A | 7/1993 | King et al. | |
| 5,383,454 A | 1/1995 | Bucholz | |
| 5,442,290 A | 8/1995 | Crooks | |
| 5,482,041 A | 1/1996 | Wilk et al. | |
| 5,558,092 A | 9/1996 | Unger et al. | |
| 5,572,132 A | 11/1996 | Pulyer et al. | |
| 5,630,426 A | 5/1997 | Eggers et al. | |
| 5,678,565 A | 10/1997 | Sarvazyan | |
| 5,699,804 A | 12/1997 | Rattner | |
| 5,704,355 A | 1/1998 | Bridges | |
| 5,727,569 A | 3/1998 | Benetti et al. | |
| 5,735,278 A | 4/1998 | Hoult et al. | |
| 5,744,971 A | 4/1998 | Chan et al. | |
| 5,758,646 A | 6/1998 | Van Der Meulen et al. | |
| 5,800,350 A * | 9/1998 | Coppleson et al. | 600/372 |
| 5,807,257 A | 9/1998 | Bridges | |
| 5,810,742 A | 9/1998 | Pearlman | |
| 5,821,410 A | 10/1998 | Xiang et al. | |
| 5,829,437 A | 11/1998 | Bridges | |
| 5,884,239 A | 3/1999 | Romanik, Jr. | |
| 5,900,618 A | 5/1999 | Anlage et al. | |
| 5,927,284 A | 7/1999 | Borst et al. | |
| 6,010,455 A | 1/2000 | Barnett et al. | |
| 6,026,323 A | 2/2000 | Skladnev et al. | |
| 6,055,452 A | 4/2000 | Pearlman | |
| 6,061,589 A | 5/2000 | Bridges et al. | |
| 6,071,239 A | 6/2000 | Cribbs et al. | |
| 6,086,534 A | 7/2000 | Kesten | |
| 6,090,041 A | 7/2000 | Clark et al. | |
| 6,109,270 A | 8/2000 | Mah et al. | |
| 6,135,968 A | 10/2000 | Brounstein | |
| 6,167,297 A | 12/2000 | Benaron | |
| 6,173,604 B1 | 1/2001 | Xiang et al. | |
| 6,233,479 B1 | 5/2001 | Haddad et al. | |
| 6,258,576 B1 | 7/2001 | Richards-Kortum et al. | |
| 6,277,083 B1 * | 8/2001 | Eggers et al. | 600/564 |
| 6,280,704 B1 | 8/2001 | Schutt et al. | |
| 6,287,302 B1 | 9/2001 | Berube | |
| 6,308,097 B1 | 10/2001 | Pearlman | |
| 6,315,981 B1 | 11/2001 | Unger | |
| 6,321,106 B1 | 11/2001 | Lemelson | |
| 6,331,166 B1 | 12/2001 | Burbank et al. | |
| 6,370,426 B1 | 4/2002 | Campbell et al. | |
| 6,375,634 B1 | 4/2002 | Carroll | |
| 6,377,841 B1 | 4/2002 | Lin et al. | |
| 6,397,095 B1 | 5/2002 | Eyuboglu et al. | |
| 6,405,733 B1 | 6/2002 | Fogarty et al. | |
| 6,500,112 B1 | 12/2002 | Khouri | |
| 6,530,944 B2 | 3/2003 | West et al. | |
| 6,546,787 B1 | 4/2003 | Schiller et al. | |
| 6,564,806 B1 | 5/2003 | Fogarty et al. | |
| 6,597,185 B1 | 7/2003 | Talanov et al. | |
| 6,671,540 B1 | 12/2003 | Hochman | |
| 6,677,755 B2 | 1/2004 | Belt et al. | |
| 6,695,782 B2 | 2/2004 | Ranucci et al. | |
| 6,699,206 B2 | 3/2004 | Burbank et al. | |
| 6,722,371 B1 | 4/2004 | Fogarty et al. | |
| 6,728,565 B2 | 4/2004 | Wendlandt | |
| 6,731,966 B1 | 5/2004 | Spigelman et al. | |
| 6,741,077 B2 | 5/2004 | Yokoyama et al. | |
| 6,747,454 B2 | 6/2004 | Belt | |
| 6,752,154 B2 | 6/2004 | Fogarty et al. | |
| 6,766,185 B2 | 7/2004 | Scott | |
| 6,813,515 B2 | 11/2004 | Hashimshony | |
| 6,840,948 B2 | 1/2005 | Albrecht et al. | |
| 6,909,084 B2 | 6/2005 | Tachi et al. | |
| 6,962,587 B2 * | 11/2005 | Johnson et al. | 606/41 |
| 7,082,325 B2 | 7/2006 | Hashimshony et al. | |
| 7,184,824 B2 | 2/2007 | Hashimshony | |
| 2001/0051774 A1 | 12/2001 | Littrup et al. | |
| 2002/0055754 A1 | 5/2002 | Ranucci et al. | |
| 2002/0059938 A1 | 5/2002 | Fogarty et al. | |
| 2002/0068880 A1 | 6/2002 | Burbank et al. | |
| 2002/0120265 A1 | 8/2002 | Fowler | |
| 2003/0045798 A1 | 3/2003 | Hular et al. | |
| 2003/0062897 A1 | 4/2003 | Belt et al. | |
| 2003/0117140 A1 | 6/2003 | Belt et al. | |
| 2003/0138378 A1 | 7/2003 | Hashimshony | |
| 2003/0171664 A1 | 9/2003 | Wendlandt | |
| 2003/0187366 A1 | 10/2003 | Hashimshony | |
| 2003/0199753 A1 | 10/2003 | Hibner et al. | |
| 2003/0216648 A1 | 11/2003 | Lizzi et al. | |
| 2003/0229343 A1 | 12/2003 | Albrecht et al. | |
| 2004/0168692 A1 | 9/2004 | Fogarty et al. | |
| 2005/0010131 A1 | 1/2005 | Burbank et al. | |
| 2005/0021019 A1 | 1/2005 | Hashimshony et al. | |
| 2005/0107717 A1 | 5/2005 | Yamamoto et al. | |
| 2006/0020279 A1 * | 1/2006 | Chauhan et al. | 606/167 |
| 2006/0253107 A1 | 11/2006 | Hashimshony et al. | |
| 2006/0264738 A1 | 11/2006 | Hashimshony et al. | |

FOREIGN PATENT DOCUMENTS

| | | |
|---|---|---|
| DE | 3637549 A1 | 5/1988 |
| EP | 0 419 235 A1 | 3/1991 |
| WO | 97/12553 A1 | 4/1997 |
| WO | 01/43630 A2 | 6/2001 |
| WO | 0165240 A1 | 9/2001 |
| WO | 03060462 A2 | 7/2003 |
| WO | 2005009200 A2 | 2/2005 |
| WO | 2005089065 A2 | 9/2005 |
| WO | 2006072947 A2 | 7/2006 |
| WO | 2006092797 A2 | 9/2006 |
| WO | 2006103665 A2 | 10/2006 |
| WO | 2007015255 A2 | 2/2007 |

OTHER PUBLICATIONS

V. Rajshekhar, "Continuous impedance monitoring during CT-guided stereotactic surgery: relative value in cycstic and solid lesions", British Journal of Neurosurgery, vol. 6, 1992, pp. 439-444.

Section on Biomedical Stochastic Physics (SBSP), "Subsurface Spectroscopy", http://www.sbsp-limb.nichd.nih.gov/html/spectroscopy.html. Apr. 1, 2005.

K. Harzbecker et al., "Thermographic thorax diagnostics", Z. Gesamte Inn. Med., Feb. 1978, 1;33(3):78-80 Abstract only (article in German).

Dexter Li, Kondrat'ev VB., "Thermography in different diagnosis of lymphostasis in the lower limbs", Vestin Khir Im I. I Grek. Jun. 1976;116(6):60-4 Abstract only (article in Russian).

Ascension Products Ltd., MiniBIRD 500 & 800, downloaded on Mar. 15, 2005, http://www.ascension-tech.com/products/minibird.php.

D. Misra et al., "Noninvasive Electrical Characterization of Materials at Microwave Frequencies Using an Open-Ended Coaxial Line: Test of an Improved Calibration Technique", IEEE Transactions on Microwave Theory & Techniques, 38:(1):8-13, 1990.

E. Burdette et al., "In Vivo Probe Measurement Technique for Determining Dielectric Properties at VHF Through Microwave Frequencies", IEEE Transactions on Microwave Theory & Techniques, MTT-28(4):414-427, 1980.

Y. Xu et al., "Measurement of Microwave Permittivity Using Open Ended Elliptical Coaxial Probes", IEEE Transactions on Microwave Theory & Techniques, 40(1): 143-150, 1992.

M. Stuchly et al., "Measurement of Radio Frequency Permittivity of Biological Tissues with an Open-Ended Coaxial Line: Part II—Experimental Results", IEEE Transactions on Microwave Theory & Techniques, MTT-30(1): 87-91, 1982.

J. Mosig et al., "Reflection of an Open-Ended Coaxial Line and Application to Nondestructive Measurement Materials", IEEE Transactions on Instrumentation and Measurement, IM-30(1):46-51, 1981.

D. Smith et al., "In Vivo Measurement of Tumor Conductiveness with the Magnetic Bioimpedance Method", IEEE Transactions on Biomedical Engineering, vol. 47, No. 10, Oct. 2000.

L. G. Brown, "A Survey of Image Registration Techniques", ACM Computing Surveys, 24(4):325-376, 1992.

M. Beard et al., "Size-Dependent Photoconductivity in CdSe Nanoparticle as Measurd by Time-Resolved Terahertz Spectroscopy", Nano Letters, 2(9), 983-987, Aug. 14, 2002, Abstract only.

M. Akerman et al., "Nanocrystal targeting in vivo", PNAS, 99(20), 12617-12621, Oct. 1, 2002.

A. J. Surowiec et al., "Dielectric Properties of Breast Carcinoma and the Surrounding Tissues", IEEE Transactions on Biomedical Engineering, vol. 35, No. 4, Apr. 1988.

H. P. Schwan, "Mechanisms responsible for electrical properties of tissues and cell suspensions", Medical Progress Through Technology, 19:163-165, 1993.

J. G. Proakis et al., "Digital Signal Processing: Principles, Algorithms, and Applications", Third Edition, Prentice Hall International Inc., Chapter 4, Table of Contents and cover page only.

"Affinity Biosensors: Techniques and Protocols", Edited by K. R. Rogers and A. Mulchandani, Humana Press, New Jersey, USA, 1998, Table of Contents pages only.

Y. Kinouchi et al., "Fast in vivo Measurement of Local Tissue Impedances Using Needle Electrodes", Med. Biol. Eng. Comput. 35(9):486-492, 1997—Abstract only.

\* cited by examiner

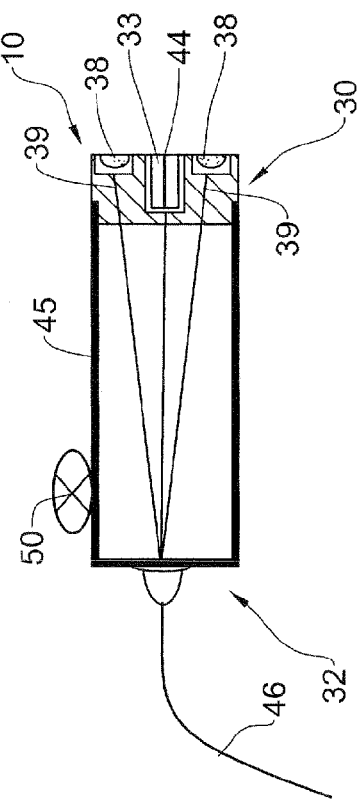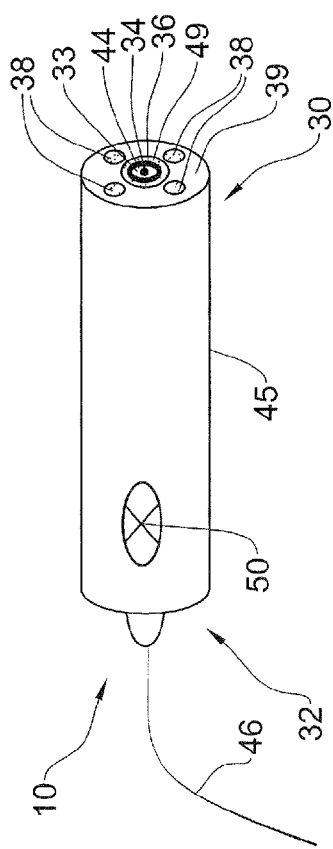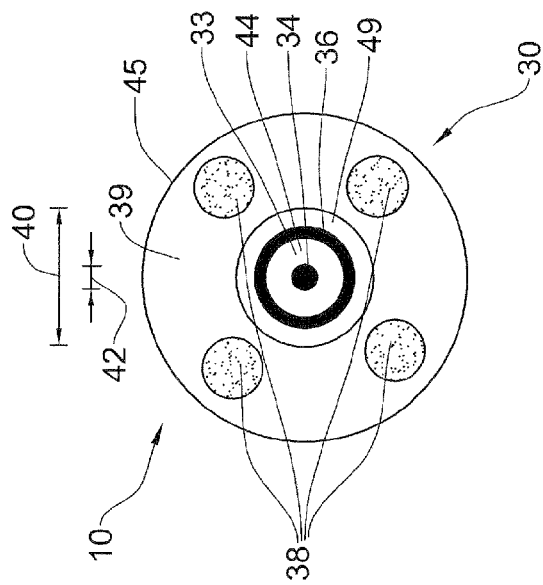

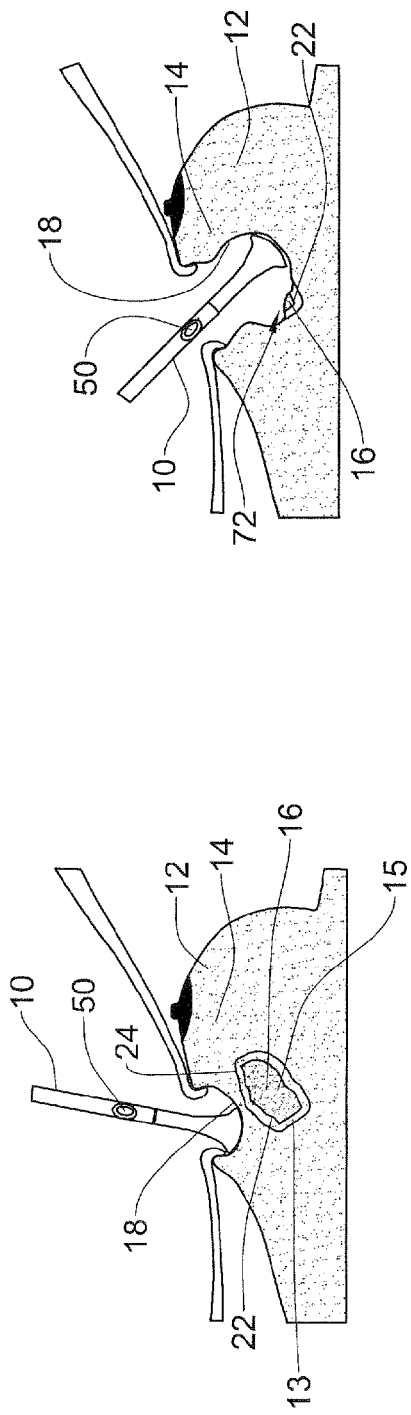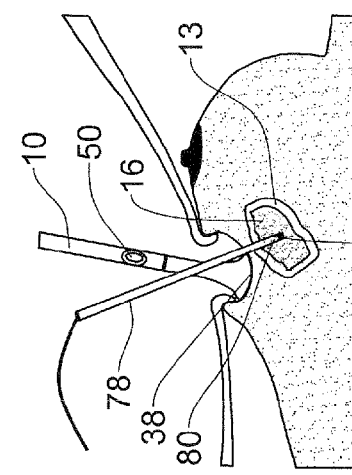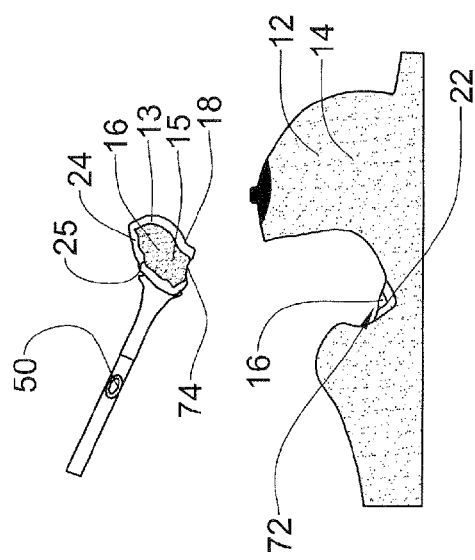
Figure 4a
Figure 4b
Figure 4c
Figure 4d

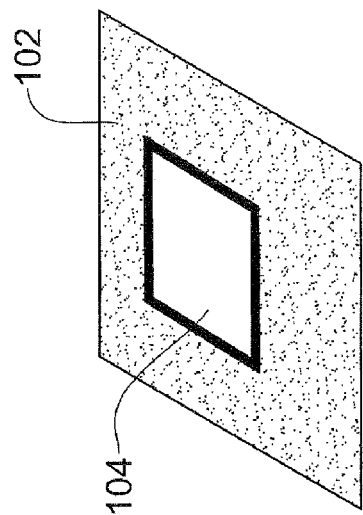
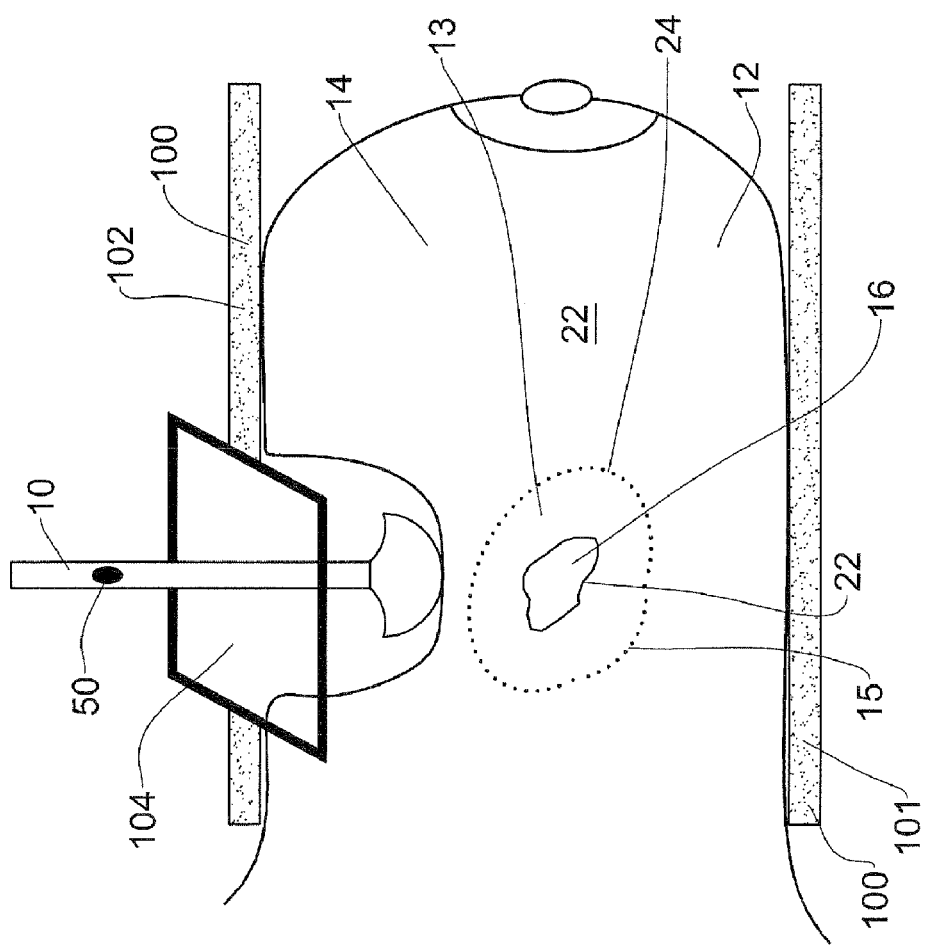

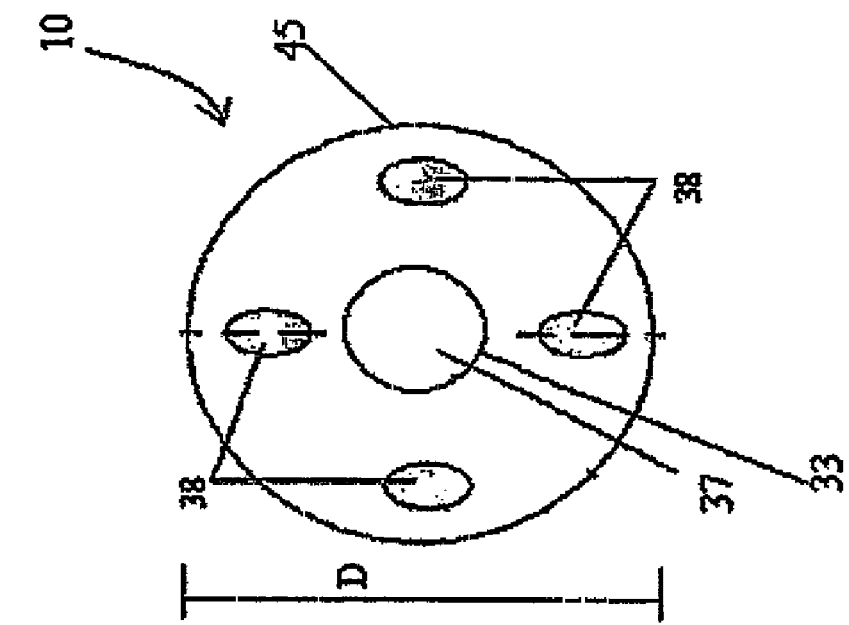
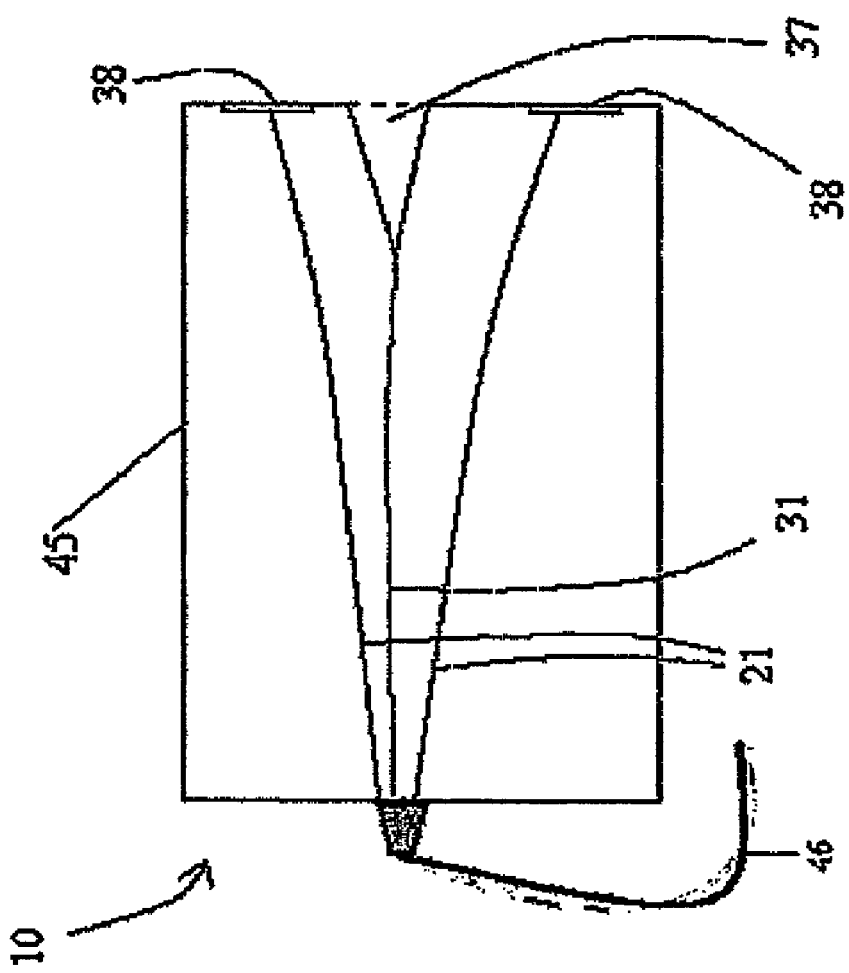
Figure 9a
Figure 9b

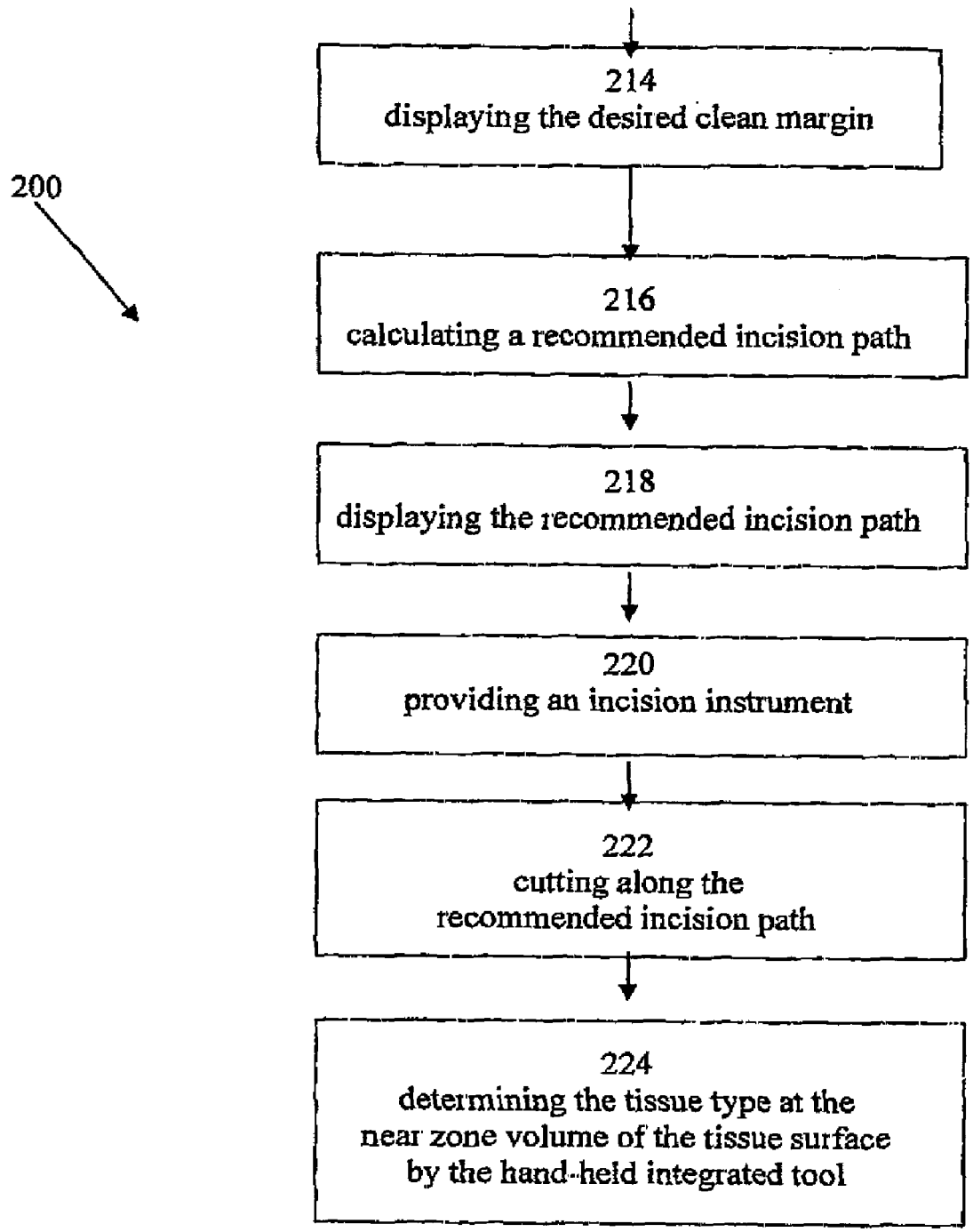

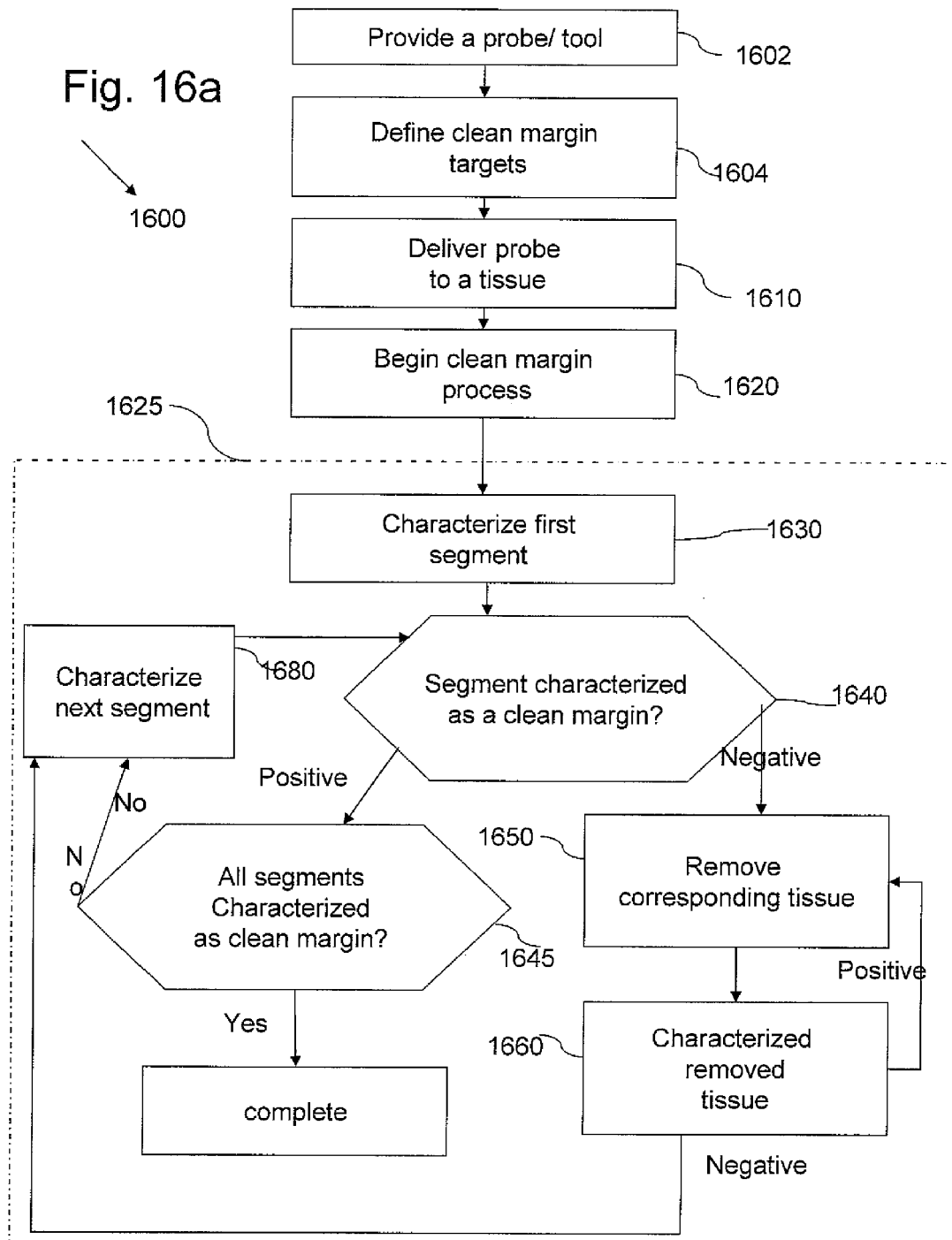

CLEAN MARGIN ASSESSMENT TOOL

This Application is a continuation-in-part of U.S. application Ser. No. 11/743,028 filed May 1, 2007, the entire contents of which being hereby incorporated by reference.

FIELD AND BACKGROUND OF THE INVENTION

The present invention relates generally to a medical tool and method for use in removal of tissues from a subject's body.

When a malignant tumor is found in a breast, the patient currently has two primary treatment options, 1) mastectomy or 2) breast conserving therapy, which means, lumpectomy, followed by radiation therapy. Generally, breast conserving therapy is indicated for patients with Stage T1 or T2 cancers, of between less then about 0.5 and about 5 cm in greatest dimension.

To localize the tumor within the breast, a radiologist may place a guide wire under x-ray or ultrasound guidance, so that the proximal tip of the guide wire, with respect to the tissue, is in the tumor. Alternatively, an imaging modality alone, for example, mammography, CT, ultrasound, or another imaging modality may be used to locate the tumor. The patient is then transported to the operating room, where the surgeon uses the guide wire, or the image, or palpation to locate the tumor in the breast and to excise a portion of tissue including the cancerous portion and a layer of healthy tissue surrounding the cancerous portion.

The layer of healthy tissue must enclose the cancerous portion, to ensure that all the malignancy has been removed. This layer is often referred to as a "clean margin". Although generally dependent on the size and shape of the malignant tumor that is being removed, a desired depth of the clean margin may range from 1 cell layer, or about 40 microns, to 10 mm.

Typically the surgeon uses a scalpel and (or) an electrosurgical cutting device to remove a tissue portion enclosing the tumor, in one piece, and manage bleeding. The removed portion is transported to the pathologist, who samples the margins, histologically, at specific and suspicious points, for example, at one or a few representative points on each face of the portion, to assess whether the cancer has been completely removed from the body. If the pathologists deems that cancer cells are too close to the edge of the portion, i.e., if he deems the margin infected, a re-excision is recommended, and the patient must undergo a second surgical procedure to remove more of the tissue.

There are several problems with conventional breast conserving therapy.

1. There are technical challenges associated with placement of the guide wire tip, and the radiologist may not place the guide wire properly through the lesion. It is particularly difficult to place the guide wire at the correct depth. Also, when the guide wire is placed under x-ray guidance, the breast is compressed. When the breast is decompressed for the surgical excision, the guide wire can move, resulting in inaccurate placement thereof. Finally, the guide wire placement procedure is uncomfortable to the patient and logistically challenging; the procedure must be coordinated with the time of surgery. Often, the easiest path for the radiologist to place the guide wire is different from the best surgical approach, so the surgeon cannot follow the guide wire down to the tumor.
2. It is difficult to estimate correctly the full extent of the disease and the exact volume of the cancerous portion of the tumor, especially with non-palpable lesions. Non-palpable lesions are similar in their properties to normal tissue, hence harder to detect by ultrasound and mammography. Thus, the guide wire may be inaccurately placed. To compensate for the imprecision in determining the extent of the disease, the surgeon must remove much more tissue than would be required if the full extent of the cancer could be imaged in real-time. This leads to a negative impact aesthetically and emotionally on the patient.

U.S. Pat. No. 6,546,787 to Schiller et al., whose disclosure is incorporated herein by reference, provides an apparatus and method for detecting a distance from a tissue edge to a malignant tissue, enclosed therein. The apparatus comprises a needle having a strain gage, mounted on one of the needles walls. Strain signals are collected as the needle is moved through the tissue. The needle is inserted at different points to allow data collection from different points within the tissue. The data is sent together with its spatial coordinates to a computerized system, which provides an image of the structure of the examined tissue.

WO Patent 9712553 to Changus et al., whose disclosures is incorporated herein by reference, provides an apparatus for marking a predetermined margin around a tumor that is contained within a healthy tissue. The apparatus includes a needle to be inserted into the patient's body towards the malignant tissue. The needle contains margin wires that are to create a cage containing the malignant tissue within it. The needle is to reach a predetermined distance of between 7 and 13 mm and preferably 10 mm from the malignant tissue before the wires are deployed to create the cage. The cage is then used to guide the surgeon performing a lumpectomy procedure, as to the portion of tissue to be excised and its location, so that the removed tissue will include the malignant tissue with a sufficient clean margin around it. The drawback of such a procedure is that it requires exact knowledge as to the location of the malignant tissue and its boundaries while creating the cage.

US Patent applications 20040168692 and 20020059938, and U.S. Pat. Nos. 6,752,154, 6,722,371, 6,564,806, 6,405,733, all to Fogarty, et al., all entitled, "Device for accurately marking tissue," and all of whose disclosures are incorporated herein by reference, describe methods and a device for fixedly yet removably marking a volume of tissue containing a suspect region for excision. Additionally they describe methods for deployment of the device and its excision along with the marked tissue volume. At least one locator element is deployed into tissue and assumes a predetermined curvilinear shape to define a tissue border containing a suspect tissue region along a path. The locator element path preferably encompasses the distal-most portion of the tissue volume, with respect to the tool, without penetrating that volume. Multiple locator elements may be deployed to further define the tissue volume along additional paths defining the tissue volume border that do not penetrate the volume. Other localization wire embodiments of the invention are disclosed in which the tissue volume may be penetrated by a portion of the device. Polar and tangential deployment configurations as well as a locator element that may be cold-formed by a die in the distal portion of the deployment tube into a permanent accurate shape are also disclosed.

US Patent application 20050010131 and U.S. Pat. Nos. 6,331,166 and 6,699,206, all to Burbank et al., all of whose disclosures are incorporated herein by reference, describe a method and apparatus for precisely isolating a target lesion in a tissue, so that there is a high likelihood the lesion is removed with a margin. The apparatus comprises a biopsy instrument having a distal end (with respect to operator) adapted for entry into the patient's body, a longitudinal shaft, and a cutting element disposed along the shaft. The cutting element is actuatable between a radially retracted and extended position. Advantageously, the instrument is rotatable about its axis in the radially extended position to isolate a desired tissue specimen from surrounding tissue by defining a peripheral margin about the tissue specimen. Once the tissue specimen is isolated, it may be segmented by further manipulation of the cutting element, after which the tissue segments are preferably individually removed from the patient's body through a cannula or the like. Alternatively, the specimen may be encapsulated and removed as an intact piece.

U.S. Pat. No. 6,840,948 to Albrecht et al, whose disclosure is incorporated herein by reference, discloses a device and method for removal of tissue lesions, for example, in the breast, the liver and the lungs. The device includes a probe housing having a rotatable RF loop cutter mounted at the distal end of the probe. The RF loop cutter can include at least one electrode supplied with an RF actuating signal for cutting tissue. A rotational drive and specimen containment sheath can also be included. Real-time imaging is preferably used with the RF loop probe to assist in placement of the probe, and to more accurately assess a desired excision volume.

Ultrasound or ultrasonography is a medical imaging technique, using high frequency sound waves in the range of about 1 to 20 MHz and their echoes. The sound waves travel in the body and are reflected by interfaces between different types of tissues, such as between a healthy tissue and a denser cancerous tissue, or between a soft tissue and a bone. The ultrasound probe receives the reflected sound waves and the associated instrumentation calculates the distances from the probe to the reflecting boundaries.

Ultrasound probes are formed of piezoelectric crystal, which produces an electric signal in response to a pressure pulse. The shape of the probe determines its field of view, and the frequency of the emitted sound determines the minimal detectable object size. Generally, the probes are designed to move across the surface of the body. However, some probes are designed to be inserted through body lumens, such as the vagina or the rectum, so as to get closer to the organ being examined.

The calculation of the distance, d, is based on the speed of sound in the tissue, v, (for example, in fat 1450 m/s, in blood 1570 m/s, in skull bone 4080 m/s, while the mean value for human soft tissue is 13 m/s, which is similar to that of water) and the time of travel, t, usually measured in microseconds. Where a single probe is used as a transmitter and receiver, the time of travel, t, refers to the time it takes the sound signal to propagate through the tissue from the ultrasound probe to the reflecting interface and back to the ultrasound probe. Thus, in a homogeneous media, the distance may be calculated according to d=v t/2.

It will be appreciated that a predetermined offset needs to be considered, due to fixed electronic and mechanical delays. For example, in cases of measurements involving direct contact transducers, the offset compensates for transit time of the sound pulse through the transducer's wear-plate and the couplant layer, and for any electronic switching time or cable delays. The offset is determined as a part of instrument calibration procedures and is necessary for high accuracy. It will be further appreciated that when a single transducer transmits and receives, there is an additional dead time, which can be overcome by using at least two transducers, one transmitting and the other receiving.

A reflectance, R, may be defined, representing the energy that is being reflected. R depends on the impedance discontinuity between the different types of tissues across the interface, or $$R=(Z_2-Z_1)^2/(Z_2+Z_1)^2,$$

where $Z_1$ is the acoustic impedance of the tissue in which the ultrasound pulse travels, and $Z_2$ is the impedance of the tissue across the interface. In general, the acoustic impedance is the product of the density of a material, $\rho$, and the speed of sound in that material, v, so that, $$Z=\rho v.$$

For tissues, which are essentially water-like, so that the speed of sound in them is essentially that of the speed of sound in water, the reflectance depends on the variation in tissue density $\rho_1$ and $\rho_2$, across the interface.

For example, in a human body, at ultrasound frequencies of several MHz, for example, 1-10 MHz, the density variation between fat and muscle tissue will lead to about 3% reflection because of the difference in ultrasonic impedance between the two types of tissue. Similarly, at these frequencies, a breast tumor, being denser than fat, will lead to a reflection of about 1%. Thus, the ultrasound technique is useful in identifying cancerous tumors. A radiologist may use the ultrasound imaging to guide a surgical tool, such as a biopsy needle or an incision instrument.

Before the early 1970's ultrasound imaging systems were able to record only the strong echoes arising from the outlines of an organ, but not the low-level echoes of the internal structure. Therefore liver scans, for instance, did not show possible carcinomas or other pathological states. In 1972 a refined imaging mode was introduced called gray-scale display, in which the internal texture of many organs became visible. In gray-scale display, low-level echoes are amplified and recorded together with the higher-level ones, giving many degrees of brightness. In consequence, ultrasound imaging became a useful tool for imaging tumors, for example, in the liver.

A development of recent years is a 3D ultrasound imaging, in which, several two-dimensional images are acquired by moving the probes across the body surface or by rotating probes, inserted into body lumens. The two-dimensional scans are then combined by specialized computer software to form 3D images.

In multiple-element probes, each element has a dedicated electric circuit, so that the beam can be "steered" by changing the timing in which each element sends out a pulse. Additionally, transducer-pulse controls allow the operator to set and change the frequency and duration of the ultrasound pulses, as well as the scan mode of the machine. A probe formed of array transducers has the ability to be steered as well as focused. By sequentially stimulating each element, the beams can be rapidly steered from the left to right, to produce a two-dimensional cross sectional image.

Contrast agents may be used in conjunction with ultrasound imaging, for example as taught by U.S. Pat. No. 6,280,704, to Schutt, et al., entitled, "Ultrasonic imaging system utilizing a long-persistence contrast agent," whose disclosure is incorporated herein by reference.

A large number of techniques, other than ultrasound, are available today for tissue characterization, to determine the presence of abnormal tissue, for example, cancerous or pre-cancerous tissue. Many of these may be used with hand-held probes. Others use miniature probes that may be inserted into a body lumen or applied in minimally invasive surgery.

One of the methods used for tissue characterization is based on measurements of the tissue's electromagnetic properties.

Commonly owned U.S. Pat. No. 6,813,515, to Hashimshony, entitled, "Method and system for examining tissue according to the dielectric properties thereof," whose disclosure is incorporated herein by reference, describes a method and system for examining tissue in order to differentiate it from other tissue, according to the dielectric properties of the examined tissue. The method includes applying an electrical pulse to the tissue to be examined via a probe formed with an open cavity such that the probe generates an electrical fringe field in examined tissue within the cavity and produces a reflected electrical pulse therefrom with negligible radiation penetrating into other tissues or biological bodies near the examined tissue; detecting the reflected electrical pulse; and comparing electrical characteristics of the reflected electrical pulse with respect to the applied electrical pulse to provide an indication of the dielectric properties of the examined tissue.

Furthermore, commonly owned U.S. Patent Application 60/641,081, entitled, "Device and Method for Tissue Characterization in a Body Lumen, by an Endoscopic Electromagnetic Probe," whose disclosure is incorporated herein by reference, discloses a device and method for tissue characterization in a body lumen, for the detection of abnormalities, using an electromagnetic probe, mounted on an endoscope. The endoscope may be designed for insertion in a body lumen, selected from the group consisting of an oral cavity, a gastrointestinal tract, a rectum, a colon, bronchi, a vagina, a cervix, a urinary tract, and blood vessels. Additionally, it may be designed for insertion in a trucar valve.

Electrical impedance imaging is another known imaging technique for detecting tumors. It involves systems in which the impedance between a point on the surface of the skin and some reference point on the body of a patient is determined. Sometimes, a multi-element probe, formed as a sheet with an array of electrical contacts is used, for obtaining a two-dimensional impedance map of the tissue, for example, the breast. The two-dimensional impedance map may be used, possibly in conjunction with other data, such as mammography, for the detection of cancer.

Rajshekhar, V. ("Continuous impedance monitoring during CT-guided stereotactic surgery: relative value in cystic and solid lesions," Rajshekhar, V., British Journal of Neurosurgery, 1992, 6, 439-444) describes using an impedance probe with a single electrode to measure the impedance characteristics of lesions. The objective of the study was to use the measurements made in the lesions to determine the extent of the lesions and to localize the lesions more accurately. The probe was guided to the tumor by CT and four measurements were made within the lesion as the probe passed through the lesion. A biopsy of the lesion was performed using the outer sheath of the probe as a guide to position, after the probe itself was withdrawn.

U.S. Pat. No. 4,458,694, to Sollish, et al., entitled, "Apparatus and method for detection of tumors in tissue," whose disclosure is incorporated herein by reference, relates to an apparatus for detecting tumors in human breast, based on the dielectric constants of localized regions of the breast tissue. The apparatus includes a probe, comprising a plurality of elements. The apparatus further includes means for applying an AC signal to the tissue, means for sensing electrical properties at each of the probe elements at different times, and signal processing circuitry, coupled to the sensing means, for comparing the electrical properties sensed at the different times. The apparatus thus provides an output of the dielectric constants of localized regions of breast tissue associated with the probe.

Similarly, U.S. Pat. No. 4,291,708 to Frei, et al., entitled, "Apparatus and method for detection of tumors in tissue," whose disclosure is incorporated herein by reference, relates to apparatus for detecting tumors in human breast tissue, by the dielectric constants of a plurality of localized regions of human breast tissue.

U.S. Pat. Nos. 6,308,097, 6,055,452 and 5,810,742, to Pearlman, A. L., entitled, "Tissue characterization based on impedance images and on impedance measurements," whose disclosures are incorporated herein by reference, describe apparatus for aiding in the identification of tissue type for an anomalous tissue in an impedance image. The device comprises: means for providing a polychromic emmitance map of a portion of the body; means for determining a plurality of polychromic measures from one or both of a portion of the body; and a display of an indication based on said plurality of polychromic measures.

Another known method of tissue characterization is by optical fluorescence spectroscopy. When a sample of large molecules is irradiated, for example, by laser light, it will absorb radiation, and various levels will be excited. Some of the excited states will return back substantially to the previous state, by elastic scattering, and some energy will be lost in internal conversion, collisions and other loss mechanisms. However, some excited states will create fluorescent radiation, which, due to the distribution of states, will give a characteristic wavelength distribution.

Some tumor-marking agents give well-structured fluorescence spectra, when irradiated by laser light. In particular, hematoporphyrin derivatives (HPD), give a well-structured fluorescence spectrum, when excited in the Soret band around 405 nm. The fluorescence spectrum shows typical peaks at about 630 and 690 nm, superimposed in practice on more unstructured tissue auto fluorescence. Other useful tumor-marking agents are dihematoporphyrin ether/ester (DHE), hematoporphyrin (HP), polyhematoporphyrin ester (PHE), and tetrasulfonated phthalocyanine (TSPC), when irradiated at 337 nm ($N_2$ laser).

U.S. Pat. No. 5,115,137, to Andersson-Engels, et al, entitled, "Diagnosis by means of fluorescent light emission from tissue," whose disclosure is incorporated herein by reference, relates to improved detection of properties of tissue by means of induced fluorescence of large molecules. The tissue character may then be evaluated from the observed large-molecule spectra. According to U.S. Pat. No. 5,115,137, the spectrum for tonsil cancer is clearly different from normal mucosa, due to endogenous porphyrins.

Similarly, U.S. Pat. No. 4,785,806, to Deckelbaum, entitled, "Laser ablation process and apparatus," whose disclosure is incorporated herein by reference, describes a process and apparatus for ablating atherosclerotic or neoplastic tissues. Optical fibers direct low power light energy at a section of tissue to be ablated to cause the section to fluoresce. The fluorescence pattern is analyzed to determine whether the fluorescence frequency spectrum is representative of normal or abnormal tissue. A source of high power, ultraviolet, laser energy directed through an optical fiber at the section of tissue is fired only when the fluorometric analysis indicates that it is directed at abnormal tissue.

Additionally, U.S. Pat. No. 4,682,594, to Mok, entitled, "Probe-and fire lasers," whose disclosure is incorporated herein by reference, describes a method and an apparatus of irradiating a treatment area within a body, such as blood vessel plaque. The method includes initially administering to the patient a non-toxic atheroma-enhancing reagent which causes the plaque to have a characteristic optical property when illuminated with a given radiation, introducing a catheter system including fiberoptic cable means into the artery such that the distal end thereof is operatively opposite the plaque site, introducing into the proximal end of the fiberoptic cable means the given radiation, photoelectrically sensing at the proximal end the characteristic optical property to generate a control signal, and directly under the control of the control signal transmitting via the cable means from the proximal end to the distal end, periodically occurring laser pulses until the characteristic optical property is no longer sensed.

U.S. Pat. No. 6,258,576, to Richards-Kortum, et al., entitled, "Diagnostic method and apparatus for cervical squamous intraepithelial lesions in vitro and in vivo using fluorescence spectroscopy," whose disclosure is incorporated herein by reference, relates to the use of multiple illumination wavelengths in fluorescence spectroscopy for the diagnosis of cancer and precancer, for example, in the cervix. In this manner, it has been possible to (i) differentiate normal or inflamed tissue from squamous intraepithelial lesions (SILs) and (ii) differentiate high grade SILs from non-high grade SILs. The detection may be performed in vitro or in vivo. Multivariate statistical analysis has been employed to reduce the number of fluorescence excitation-emission wavelength pairs needed to re-develop algorithms that demonstrate a minimum decrease in classification accuracy. For example, the method of the aforementioned patent may comprise illuminating a tissue sample with electromagnetic radiation wavelengths of about 337 nm, 380 nm and 460 nm, to produce fluorescence; detecting a plurality of discrete emission wavelengths from the fluorescence; and calculating from the emission wavelengths a probability that the tissue sample belongs in particular tissue classification.

Commonly owned U.S. Patent Application 2003/01383786, to Hashimshony, entitled, "Method and apparatus for examining tissue for predefined target cells, particularly cancerous cells, and a probe useful for such method and apparatus," whose disclosure is incorporated herein by reference, teaches a method apparatus and probe for examining tissue and characterizing its type according to measured changes in optical characteristics of the examined tissue. In a preferred embodiment of this method the tissue to be examined is subject to a contrast agent containing small particles of a physical element conjugated with a biological carrier selectively bindable to the target cells. Additionally, energy pulses are applied to the examined tissue, and the changes in impedance and/or the optical characteristics produced by the applied energy pulses are detected and utilized for determining the presence of the target cells in the examined tissue. Furthermore, in a preferred embodiment, the applied energy pulses include laser pulses, and the physical element conjugated with a biological carrier is a light-sensitive semiconductor having impedance which substantially decrease in the presence of light. Moreover, the same probe used for detecting the targeted cells, may also be used for destroying the cells so targeted.

Optical reflectance spectroscopy may also be used. Its application for tissue characterization is described, for example, in http://www.sbsp-limb.nichd.nih.gov/html/spectroscopy.html, downloaded on Mar. 15, 2005. It describes an optical reflectance spectroscopy (ORS) device for measuring the thickness of the epithelial layer, and an evaluation technique based on oblique angle reflectance spectroscopy that allows assessment of the scattering and absorption properties of the epithelium and stroma, thus providing information on chronic oral epithelial tissue inflammation, which is considered a potential diagnostic precursor to oral cancer.

Another known method for tissue characterization is magnetic resonance imaging (MRI), which is based on the absorption and emission of energy in the radio frequency range of the electromagnetic spectrum, by nuclei having unpaired spins.

Conventional MRI is a large-apparatus, for whole body imaging, having:

i. a primary magnet, which produces the $B_o$ field for the imaging procedure;

ii. gradient coils for producing a gradient in $B_o$;

iii. an RF coil, for producing the $B_1$ magnetic field, necessary to rotate the spins by 90° or 180° and for detecting the MRI signal; and iv. a computer, for controlling the components of the MRI imager.

Generally, the magnet is a large horizontal bore superconducting magnet, which provides a homogeneous magnetic field in an internal region within the magnet. A patient or object to be imaged is usually positioned in the homogeneous field region located in the central air gap for imaging. A typical gradient coil system comprises an anti-Helmholtz type of coil. These are two parallel ring shaped coils, around the z axis. Current in each of the two coils flows in opposite directions creating a magnetic field gradient between the two coils.

The RF coil creates a B1 field, which rotates the net magnetization in a pulse sequence. The RF coils may be: 1) transmit and receive coils, 2) receive only coils, and 3) transmit only coils.

As described hereinabove, the MRI relies on a magnetic field in an internal region within the magnet. As such, it is unsuitable as a handheld probe or an endoscopic probe, because the tissue to be imaged has to be in the internal region of the imager, This problem has been resolved by U.S. Pat. No. 5,572,132, to Pulyer, et al., entitled, "MRI probe for external imaging," whose disclosure is incorporated herein by reference, which describes an MRI spectroscopic probe having an external background magnetic field B0 (as opposed to the internal background magnetic filed of the large horizontal bore superconducting magnet.). Thus, an MRI catheter for endoscopical imaging of tissue of the artery wall, rectum, urinal tract, intestine, esophagus, nasal passages, vagina and other biomedical applications may be constructed. The probe comprises (i) a miniature primary magnet having a longitudinal axis and an external surface extending in the axial direction, and (ii) a RF coil surrounding and proximal to said surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

Additionally, commonly owned US Patent Application 2005/0021019 to Hashimshony et al., entitled "Method and apparatus for examining substance, particularly tissue, to characterize its type," whose disclosure is incorporated herein by reference, describes a method and apparatus for examining a substance volume to characterize its type, by: applying a polarizing magnetic field through the examined substance: applying RF pulses locally to the examined substance volume such as to invoke electrical impedance (EI) responses signals corresponding to the electrical impedance of the substance, and magnetic resonance (MR) responses signals corresponding to the MR properties of the substance; detecting the EI and MR response signals; and utilizing the detected response signals for characterizing the examined substance volume type.

Contrast agents may be used in conjunction with MRI. For example, U.S. Pat. No. 6,315,981 to Unger, entitled, "Gas filled microspheres as magnetic resonance imaging contrast agents," whose disclosure is incorporated herein by reference, describes the use of gas filled microspheres as contrast agents for MRI.

Temperature imaging for locating and detecting neoplastic tissue is also known. In the 1950's, it was discovered that the surface temperature of skin in the area of a malignant tumor exhibited a higher temperature than that expected of healthy tissue. Thus, by measuring body skin temperatures, it became possible to screen for the existence of abnormal body activity such as cancerous tumor growth. With the development of liquid crystals and methods of forming temperature responsive chemical substrates, contact thermometry became a reality along with its use in medical applications. Devices employing contact thermometry could sense and display temperature changes through indicators which changed colors, either permanently or temporarily, when placed in direct physical contact with a surface such as skin, reflecting a temperature at or near the point of contact. An abnormal reading would alert a user to the need for closer, more detailed examination of the region in question. However, the art in this area has been directed primarily at sensing and displaying temperatures on exterior skin surfaces. Thus, for example, U.S. Pat. No. 3,830,224, to Vanzetti et al., whose disclosure is incorporated herein by reference, disclosed the placement of temperature responsive, color changing liquid crystals at various points in a brassiere for the purpose of detecting the existence of breast cancer, while U.S. Pat. RE 32,000, to Sagi, entitled, "Device for Use in Early Detection of Breast Cancer," whose disclosure is incorporated herein by reference, disclosed the use of radially arranged rows of temperature responsive indicators, deposited on a disc for insertion into the breast-receiving cups of a brassiere for the same purpose.

U.S. Pat. No. 6,135,968, to Brounstein, entitled, "Differential temperature measuring device and method", whose disclosure is incorporated herein by reference, describes a device and method for sensing temperatures at internal body locations non-surgically accessible only through body orifices. The device is particularly useful in medical applications such as screening for cancer and other abnormal biological activity signaled by an increase in temperature at a selected site. As applied to prostate examinations, the device is temporarily, adhesively affixed to a user's fingertip or to a mechanical probe. In the preferred embodiment, the device includes two temperature-sensing elements, which may include a plurality of chemical indicators. Each indicator changes color in response to detection of a predetermined particular temperature. When properly aligned and installed, the first element is located on the palmar surface of the fingertip while the second element is located on the dorsal surface of the fingertip. After an examination glove has been donned over the fingertip carrying the device, a prostate examination is performed during which the first element is brought into constant but brief contact with the prostate region and the second element is similarly, simultaneously brought into contact with a dermal surface opposing the prostate region. Upon withdrawal of the fingertip from the rectum and removal of the glove, the two temperature sensing elements may be visually examined in order to determine the temperatures detected by each one. A significant difference in observed temperatures indicates the possibility of abnormal biological activity and the need for further diagnostic or medical procedures.

Infrared thermography is a temperature imaging technique, which measures thermal energy emitted from the body surface without contact, quickly and dynamically, and produces a temperature image for analysis. Harzbecker K, et al. report, based on thermic observations in 63 patients and a control experiment in 15 persons, on experiences with thermography in the diagnosis of diseases, which are localized more profoundly in the thoracic cavity. (Harzbecker K, et al., "Thermographic thorax diagnostics," Z Gesamte Inn Med. 1978 Feb. 1; 33(3):78-80.)

Similarly, Dexter L I, Kondrat'ev V B. report data concerning the use of lymphography and thermography for the purpose of establishing a differential diagnosis in 42 patients with edema of the lower limbs of a different origin. A comparative estimation of different methods of the differential diagnosis indicated the advantages of infrared thermography. (Dexter L I, Kondrat'ev V B., "Thermography in differential diagnosis of lymphostasis in the lower limbs," Vestn Khir Im I I Grek. 1976 June; 116(6):60-4.)

Various means for minimally invasive surgical removal, of a breast tumor and other tumors in a soft tissue are known.

For example, U.S. Pat. No. 6,375,634, to Carroll, entitled, apparatus and method to encapsulate, kill and remove malignancies, including selectively increasing absorption of x-rays and increasing free-radical damage to residual tumors targeted by ionizing and non-ionizing radiation therapy", whose disclosure is incorporated herein by reference, describes a coaxial bipolar needle electrode for applying radio-frequency diathermal heat.

U.S. Pat. No. 6,840,948 to Albrecht, et al. entitled, "Device for removal of tissue lesions," whose disclosure is incorporated herein by reference, describes an excisional biopsy device and method for excision and removal of neoplasms under real-time image guidance with minimal disruption of normal tissue while providing an optimal specimen to assess the completeness of the excision. The device and method are minimally invasive, and are used to remove cancerous lesions from soft tissue, including breast tissue, and are a less invasive alternative to open lumpectomy. The invention provides an RF loop for excision and removal of breast lesions which promotes hemostasis during excision through electrosurgical coagulation of blood vessels and channels to supply pressure and hemostatic fluids to the tissue cavity.

The method includes is as follows: The mass is localized, and the tunneling trajectory is determined. The skin is excised, and tunneling is begun by activating and using the semi-circular RF tunneling electrode. After tunneling is completed, but prior to cutting a sphere, the coordinates of the excision specimen are confirmed, preferably with the assistance of computer aided imaging and guidance technology. The semi-circular rotational electrode blade of the RF loop is then activated and used to cut the sphere, and is rotated by the drive electrical cables attached to the power drive. Simultaneously, the tissue is immobilized and any blood is aspirated by vacuum. As the RF loop is rotated, it pulls along the containment sheath or bag that surrounds the spherical specimen. After the sphere is fully cut, the RF loop is held in place and the containment sheath is pulled taught around the sphere by a draw cord to reduce the sphere's volume to aid in its removal. The device and sphere are then removed from the body simultaneously.

US Patent Application 20020120265, to Fowler, entitled, "Symmetric conization electrocautery device," whose disclosure is incorporated herein by reference, describes a tissue electrocautery device that accommodates anatomical structures lying at more than one longitudinal axes. Such a circumstance is encountered when attempting to perform symmetric tissue electrocautery of an endocervical canal where the longitudinal axis of the vaginal vault is at an angle to the longitudinal axis of the endocervical canal. The device of the present invention uses a hollow housing, elongate along a first longitudinal axis, having a proximal portion with a proximal end and a distal end, and includes a distal portion from the distal end. The distal portion is elongate along a second longitudinal axis and pivotable in relation to the proximal portion at a selectable angle to the first longitudinal axis. Within the housing is a rotatable electrically conducting mechanism, adapted to conduct electrocautery energy from an electrode proximal to the housing proximal portion to a coupling proximate the distal portion, while rotating the coupling with a removable handle proximal to the housing proximal portion. The electrical energy is delivered to an electrocautery head, carrying an electrocautery wire, operably electrically engageable with the coupling and rotatable around a longitudinal axis parallel the second longitudinal axis, electrocauterizing tissue of a human patient while rotating around its longitudinal axis.

In spite of these works, clean removal of malignancies, surrounded by definite and sufficient clean margins, remains an elusive goal.

GENERAL DESCRIPTION OF THE INVENTION

The present invention provides a novel medical device including one or more tissue-type sensors for identifying clean margin within a periphery region of a tissue portion under examination. This enables removal of said tissue portion and/or removal of tissues adjacent to (surrounding) said tissue portion.

The present invention in its one aspect provides a hand-held, integrated tool, having a tissue-type sensor, for determining the tissue type at a near zone volume of a tissue surface, and a distance-measuring sensor, for determining the distance to an interface with another tissue type. The tool is operable for (i) confirming an existence of a clean margin of healthy tissue around a malignant tumor, which is being removed, and (ii) determining the width of the clean margin, wherein both are performed in real time, while the malignant tumor is being removed. The tissue-type sensor may be selected from the group of a sensor for tissue electromagnetic properties, a dielectric sensor, an impedance sensor, a sensor for optical fluorescence spectroscopy, a sensor for optical reflectance spectroscopy, an MRI sensor, an RF sensor, an MW sensor, a temperature sensor, and infrared thermography sensor, or another tissue-characterization sensor, as known. The distance-measuring sensor may be an ultrasound transducer, an MRI probe, an invasive needle with a strain or pressure gauge, or another tissue distance measuring sensor, as known. The integrated tool may further include a position tracking device and an incision instrument. The soft tissue may be held within a fixed frame, while the tumor is being removed. Additionally a method for malignant tumor removal is provided, comprising, fixing the soft tissue within a frame, performing imaging with the hand-held, integrated tool, from a plurality of locations and orientations around the soft tissue, reconstructing a three-dimensional image of the soft tissue and the tumor within, defining a desired clean margin on the reconstructed image, calculating a recommended incision path, displaying the recommended path on the reconstructed image, and cutting the tissue while determining its type, at the near zone volume of the incision surface, by the hand-held integrated tool. The method may further include continuously imaging with the cutting, continuously correcting the reconstructed image and the recommended incision path, and continuously determining the tissue type, at the near zone volume of the incision surface.

In accordance with one aspect of the present invention, there is provided an integrated tool, for clean-margin assessment, comprising:

a structure, which defines a proximal end with respect to a tissue and which is adapted for placement proximally to the tissue;

a tissue-type sensor, mounted on the structure, for determining a tissue type at a near zone volume of a tissue surface; and a distance-measuring sensor, mounted on the structure, for determining a distance between the tissue surface and an interface with another tissue type, wherein the integrated tool is configured as a hand-held tool.

In accordance with an additional aspect of the present invention, the another tissue type is a cancerous tissue, and the integrated tool may be used to assess:

whether the tissue type at the near zone volume of the tissue surface is healthy; and the distance between the tissue surface and an interface with the cancerous tissue.

In accordance with an additional aspect of the present invention, the integrated tool is adapted for operation in tandem with a surgical tool, for a real-time correction of a clean margin, where necessary.

In accordance with an additional aspect of the present invention, the integrated tool includes an incision instrument, integrated therewith, for a real-time correction of a clean margin, where necessary.

In accordance with an additional aspect of the present invention, the incision instrument may be selectively retracted and selectively deployed.

In accordance with an additional aspect of the present invention, the incision instrument is a diathermal incision instrument.

In accordance with an additional aspect of the present invention, the tissue-type sensor is selected from the group consisting of a sensor for tissue electromagnetic properties, a dielectric sensor, an impedance sensor, a sensor for optical fluorescence spectroscopy, a sensor for optical reflectance spectroscopy, an MRI sensor, an RF sensor, an MW sensor, a temperature sensor, and infrared thermography sensor.

In accordance with an additional aspect of the present invention, the tissue-type sensor is a dielectric-property sensor, formed substantially as a coaxial cable.

In accordance with an additional aspect of the present invention, the tissue surface is selected from the group consisting of a skin, a tissue lumen, and an incision surface.

In accordance with an additional aspect of the present invention, the distance-measuring sensor is an ultrasound transducer.

In accordance with an additional aspect of the present invention, the distance-measuring sensor is formed of two ultrasound transducers.

In accordance with an additional aspect of the present invention, the distance-measuring sensor is formed of an array of ultrasound transducers, which may be selectively steered.

In accordance with an additional aspect of the present invention, the distance-measuring sensor is selected from the group consisting of a strain gauge and a pressure sensor.

In accordance with an additional aspect of the present invention, the distance-measuring sensor is an MRI probe.

In accordance with an additional aspect of the present invention, the integrated tool is operative with a guide wire, wherein a proximal tip of the guide wire, with respect to the tissue, is placed within the another tissue type.

In accordance with an alternative aspect of the present invention, the integrated tool is operative with a guide wire, wherein a proximal tip of the guide wire, with respect to the tissue, is placed in close proximity with the another tissue type.

In accordance with an additional aspect of the present invention, the integrated tool is operative with a guide wire, wherein the distance-measuring sensor is an ultrasound transducer, and the guide wire further includes a guide wire ultrasound transducer, at a proximal tip thereof, with respect to the tissue, for emitting ultrasound signals, indicative of the proximal-tip distance from the integrated tool.

In accordance with an additional aspect of the present invention, the integrated tool is operative with a guide wire, wherein the distance-measuring sensor is an ultrasound transducer, and the guide wire further includes a guide wire ultrasound transducer, at a proximal tip thereof, with respect to the tissue, for emitting ultrasound signals, indicative of the proximal-tip position with respect to the integrated tool, by triangulation.

In accordance with an additional aspect of the present invention, the integrated tool includes a position-tracking device.

In accordance with an additional aspect of the present invention, the position-tracking device is correlated with a coordinate system of a fixed frame, within which, the tissue is held fixed in place.

In accordance with another aspect of the present invention, there is provided a system for clean-margin assessment, comprising:
  a hand-held, integrated tool, for clean-margin assessment, which comprises:
    a structure, which defines a proximal end with respect to a tissue and which is adapted for placement proximally to the tissue;
    a tissue-type sensor, mounted on the structure, for determining a tissue type at a near zone volume of a tissue surface; and
    a distance-measuring sensor, mounted on the structure, for determining a distance between the tissue surface and an interface with another tissue type;
  a computerized system, which comprises:
  a tissue-type-sensor analyzer, associated with the tissue-type sensor;
  a distance-measuring-sensor analyzer, associated with the distance-measuring sensor;
  an output device, which provides output of measurements by the tissue-type sensor and the distance-measuring sensor.

In accordance with an additional aspect of the present invention, the system includes a fixed frame for holding the tissue therein.

In accordance with an additional aspect of the present invention, the system includes a position-tracking device and a position-tracking-device analyzer.

In accordance with an additional aspect of the present invention, the system includes a computer.

In accordance with yet another aspect of the present invention, there is provided a system for clean-margin assessment, comprising:

a fixed frame for holding a tissue therein, the frame defining a coordinate system;
  a hand-held, integrated tool, for clean-margin assessment, which comprises:
    a structure, which defines a proximal end with respect to the tissue and which is adapted for placement proximally to the tissue;
    a tissue-type sensor, mounted on the structure, for determining a tissue type at a near zone volume of a tissue surface;
    an imager, operative as a distance-measuring sensor, mounted on the structure, for determining a distance between the tissue surface and an interface with another tissue type; and
    a position-tracking device, mounted on the structure and correlated with the coordinate system;
  a computerized system, which comprises:
    a tissue-type-sensor-analyzer, associated with the tissue-type sensor;
    a distance-measuring-sensor analyzer, associated with the distance-measuring sensor;
    a position-tracking-device analyzer, associated with the position-tracking device;
    a computer, for receiving data from the tissue-type-sensor analyzer, the distance-measuring-sensor analyzer, and the position-tracking-device analyzer, and performing analysis thereof;
  an output device, associated with the computer.

In accordance with still another aspect of the present invention, there is provided a method of clean-margin assessment, comprising:
  providing a hand-held, integrated tool, for clean-margin assessment, which comprises:
    a structure, which defines a proximal end with respect to a tissue and which is adapted for placement proximally to the tissue;
    a tissue-type sensor, mounted on the structure, for determining a tissue type at a near zone volume of a tissue surface; and
    a distance-measuring sensor, mounted on the structure, for determining a distance between the tissue surface and an interface with another tissue type;
  determining the tissue type at the near zone volume of the tissue surface; and
  determining the distance between the tissue surface and the interface with the another tissue type.

In accordance with yet another aspect of the present invention, there is provided a method of clean-margin assessment, comprising:
  providing a hand-held, integrated tool, for clean-margin assessment, which comprises:
    a structure, which defines a proximal end with respect to a tissue and which is adapted for placement proximally to the tissue;
    a tissue-type sensor, mounted on the structure, for determining a tissue type at a near zone volume of a tissue surface; and
    a non-invasive imager, mounted on the structure; and
    a position-tracking device, mounted on the structure;
  fixing the tissue within a fixed frame, which defines a coordinate system;
  imaging the tissue, from at least two locations and orientations, by the hand-held, integrated tool;
  reconstructing a three dimensional image of the tissue;
  displaying the three dimensional image of the tissue;
  defining a desired clean margin around another tissue type;
  displaying the desired clean margin;

calculating a recommended incision path;
displaying the recommended incision path;
providing an incision instrument;
cutting along the recommended incision path; and
determining the tissue type at the near zone volume of the tissue surface, by the hand-held, integrated tool.

In accordance with an additional aspect of the present invention, the method includes:
continuously imaging the tissue, from different locations and orientations along the tissue surface, by the hand-held, integrated tool;
continuously correcting the recommended incision path; and
continuously displaying the continuously corrected recommended incision path.

In accordance with an additional aspect of the present invention, the method includes continuously determining the tissue type, at the near zone volume of the incision surface, by the hand-held, integrated tool.

According to yet further aspect of the invention, there is provided a system for use in clean-margin assessment, the system comprising:
a) a medical tool comprising a tissue-type sensor unit configured for placing proximal to a tissue portion under characterization, said tissue-type sensor unit comprising at least one tissue type sensor configured and operable for determining a type of the tissue within the surface of said tissue portion and generating data indicative thereof;
b) a computerized system connectable to the medical tool and comprising: an analyzer utility, associated with the tissue-type sensor unit for receiving and analyzing data generated by tissue-type sensor unit, and determining whether a clean margin of healthy tissue exists in a periphery region of the tissue portion, and generating data indicative of the analysis results; and an output device, which provides output data corresponding to said data generated by the analyzer utility,
the system thereby enabling removal of additional tissues at locations adjacent to the periphery region of said tissue portion, upon detecting that there is no clean margin in the periphery region of the characterized tissue portion thus, confirming an existence of a clean margin of healthy tissue around an abnormal tissue.

The system preferably also includes a data presentation utility, such as a display for presenting the output data to a user.

In some embodiments of the invention, the system includes a fixed frame for holding the tissue therein.

In some embodiments of the invention, the system includes a position-tracking device and a position-tracking-device analyzer.

The medical tool includes a structure, which defines a proximal end with respect to the tissue portion and which is adapted for placement proximally to the tissue.

The system may include a distance-measuring sensor, which may include at least one ultrasound transducer, or an array of ultrasound transducers configured to be selectively steered. Generally, the distance-measuring sensor may include a strain gauge, an MRI probe and a pressure sensor. The distance-measuring sensor may be integral within the medical tool.

The tissue-type sensor may include a sensor for tissue electromagnetic properties, a dielectric sensor, an impedance sensor, a sensor for optical fluorescence spectroscopy, a sensor for optical reflectance spectroscopy, an MRI sensor, an RF sensor, an MW sensor, a temperature sensor, and/or infrared thermography sensor.

The tissue type sensor may be configured and operable for determining a type of the tissue within a near zone volume of the surface of the tissue portion and generating data indicative thereof.

According to yet another broad aspect of the invention, there is provided a medical tool for use in a clean margin assessment system for determining existence of a clean margin of healthy tissues in a periphery region of a tissue portion, the medical tool comprising: a tissue-type sensor unit comprising at least one tissue-type sensor configured and operable to determine a type of the tissue at various locations along the tissue portion surface and generating data indicative of existence of a clean margin of healthy tissue in a periphery region of the tissue portion, thereby enabling to decide about removal of additional tissues at locations adjacent to said periphery region of said tissue portion.

The tool may be adapted for operation in tandem with a surgical tool, for a real-time correction of a clean margin. The tool may include an incision instrument configured and operable for a real-time correction of a clean margin. The incision instrument may be configured to be selectively retracted and selectively deployed; or may be a diathermal incision instrument.

The tissue-type sensor may include at least one of the following: a sensor for tissue electromagnetic properties, a dielectric-property sensor (e.g. formed substantially as a coaxial cable), an impedance sensor, a sensor for optical fluorescence spectroscopy, a sensor for optical reflectance spectroscopy, an MRI sensor, an RF sensor, an MW sensor, a temperature sensor, and infrared thermography sensor.

According to yet another aspect of the invention, there is provided a method for use in removal of tissue from a subject's body, the method comprising: examining a tissue portion, determining a tissue type at the surface of said tissue portion, and generating tissue characterizing data; analyzing said tissue characterizing data, determining existence of a clean margin of healthy tissues in a periphery region of said tissue portion, and generating output data indicative thereof, thereby enabling to decide about removal of tissue at locations adjacent to said periphery region of said tissue portion for providing a clean margin of healthy tissue around an abnormal tissue.

According to yet further aspect of the invention, there is provided a method for use in clean-margin assessment of a first tissue type around a second tissue type in a tissue portion, said method comprising:
a) applying to the tissue portion to be examined a hand-held medical tool comprising a tissue-type sensor unit configured to determine the type of the tissue at various locations along the tissue portion surface and generate data indicative thereof;
b) operating the medical tool for determining the tissue type at various locations along said tissue portion surface; and
c) analyzing data generated by the medical tool and providing output data indicative of existence of a clean margin of a first tissue type in a periphery region of said tissue potion, thereby enabling to decide about removal of additional tissues at locations adjacent to said periphery region of the characterized tissue portion.

The invention also provides a method for providing a clean-margin of healthy tissue around a malignant tumor, the method comprising: characterizing a tissue segment of a tissue surface; recording tissue segment margin status; determining whether the tissue segment is characterized as clean margin thereby enabling removal of tissue segments which are adjacent/correspond to the tissue segment which were not characterized as clean margin.

The invention in its yet further aspect provides a method for providing a clean-margin of healthy tissue around a malignant tumor, the method comprising: providing a device for holding and characterizing the tissue, said device comprising a housing configured for receiving and holding a tissue, and at least one tissue-type sensor mounted on the housing and configured for characterizing the tissue type; inserting the tissue portion into the device; characterizing all tissue segments of the tissue portion surface; recording tissue segments margin status; determining whether all tissue segments are characterized as clean margin; removing tissue segments which are adjacent/correspond to tissue segments which were not characterized as clean margin until the margin status of all the characterized tissue segments is clean.

In yet further aspect of the invention, there is provided a device for holding and characterizing a tissue during a clean-margin assessment process, said device comprises: a housing configured for receiving and holding the tissue; at least one tissue-type sensor, mounted on the housing, for characterizing the tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

According to yet further broad aspect of the invention, there is provided a method for use in providing a clean-margin of healthy tissue around an abnormal tissue, the method comprising: characterizing a tissue segment of a tissue surface to determine and record the tissue segment margin status; analyzing the tissue segment margin status for identifying whether it corresponds to clean margin, thereby enabling removal of tissue segments which are adjacent or correspond to the tissue segments which were not identified as clean margin.

The invention also provides a method for use in providing a clean-margin of healthy tissue around an abnormal tissue, the method comprising: providing a device for characterizing the tissue, said device comprising a housing configured to be enclosed by said tissue, and at least one tissue-type sensor mounted on the housing and configured for characterizing the tissue type, and providing a mechanism configured to attach said tissue to the housing; surrounding or enclosing the device by said tissue; characterizing all tissue segments of the tissue portion surface; recording tissue segments margin status; identifying whether all tissue segments correspond to clean margin; removing tissue segments which are adjacent or correspond to tissue segments which were not identified as clean margin until the margin status of all the characterized tissue segments is clean.

According to yet another aspect of the invention, there is provided a device for holding a tissue portion in a tissue characterization procedure, the device comprising: a housing configured for carrying one or more tissue-type sensors, and configured to be surrounded by the tissues portion to hold said tissue portion by suction; and a mechanism configured and operable to attach said tissue to the housing by causing the tissue to wrap the surface of the housing.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a-2c schematically illustrate an isometric view, a frontal view, and a cross-sectional view of the integrated tool for clean-margin assessment, in accordance with the present invention;

FIGS. 4a-4d further illustrate the operational manner of the integrated tool for clean-margin assessment, in accordance with the present invention;

FIGS. 8a-8b schematically illustrate the integrated tool for clean-margin assessment, operative with a frame for fixing a soft tissue, in accordance with a preferred embodiment of the present invention;

FIGS. 9a and 9b schematically illustrate the integrated tool for clean-margin assessment, wherein the tissue-type sensor is formed as a horn antenna, for RF or MW, in accordance with still another embodiment of the present invention;

FIGS. 15a and 15b show the top and cross sectional views, respectively, of a tissue part including a tissue portion under characterization or from which a tissue portion have been removed; and FIG. 15c shows more specifically a peripheral region or surrounding region of said tissue portion;

FIGS. 16a and 16b illustrate flowcharts of a method of the present invention for providing a clean margin of healthy tissue around a malignant tumor or abnormal tissue;

DESCRIPTION OF EMBODIMENTS

Figure 1A:
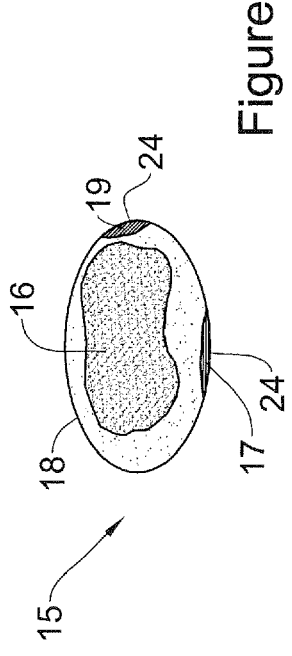
FIGS. 1a-1f schematically illustrate the application of an integrated tool for clean-margin assessment to a soft tissue that contains a cancerous tissue within and the principles of clean-margin assessment, in accordance with the present invention.

The present invention is of an integrated tool having a tissue-type sensor, for determining the tissue type at a near zone volume of a tissue surface, and a distance-measuring sensor, for determining the distance to an interface with another tissue type. The tool is operable for (i) confirming an existence of a clean margin of healthy tissue around a malignant tumor, which is being removed, and (ii) determining the width of the clean margin, wherein both are performed in real time, while the malignant tumor is being removed. The tissue-type sensor may be selected from the following: a sensor for tissue electromagnetic properties, a dielectric sensor, an impedance sensor, a sensor for optical fluorescence spectroscopy, a sensor for optical reflectance spectroscopy, an MRI sensor, an RF sensor, an MW sensor, a temperature sensor, and infrared thermography sensor, or another tissue-characterization sensor, as known. The distance-measuring sensor may include at least one of the following: an ultrasound transducer, an MRI probe, an invasive needle with a strain or pressure gauge, or another tissue distance measuring sensor, as known. The integrated tool may further include a position tracking device and an incision instrument. The soft tissue may be held within a fixed frame, while the tumor is being removed. Additionally a method for malignant tumor removal is provided, comprising, fixing the soft tissue within a frame, performing imaging with the hand-held, integrated tool, from a plurality of locations and orientations around the soft tissue, reconstructing a three-dimensional image of the soft tissue and the tumor within, defining a desired clean margin on the reconstructed image, calculating a recommended incision path, displaying the recommended path on the reconstructed image, and cutting the tissue while determining its type, at the near zone volume of the incision surface, by the hand-held integrated tool. The method may further include continuously imaging with the cutting, continuously correcting the reconstructed image and the recommended incision path, and continuously determining the tissue type, at the near zone volume of the incision surface.

Before explaining at least one embodiment of the invention in detail, it should be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1a-1f schematically illustrate the principles of clean margin assessment and the application of a hand-held, integrated tool 10 for clean-margin assessment, in accordance with some embodiments of the present invention.

The principles of clean margin assessment may be understood using the examples of FIGS. 1a-1d. These illustrate tissue portions 15 which have been removed from the body. These portions include a first tissue type of healthy tissue 14, enclosing or partly enclosing a second tissue type of cancerous or otherwise abnormal tissue 16. A tissue surface 18, which is generally the incision surface, bounds each of the tissue portions 15.

However, it will be appreciated that the tissue surface 18 may be a skin, a body lumen, or an incision surface; either an arbitrary incision surface, or an incision surface contouring an organ and an anatomical feature.

As seen in FIG. 1a, the incision surface 18 has a positive margin 27 at a location 19. This means that cancerous or otherwise abnormal cells have reached the surface 18 or the near zone volume of the surface 18, at the location 19. This may happen when the incision was performed right through the cancerous or abnormal second tissue type 16. Alternatively, this may happen when the incision is performed at the interface between the first and second tissue types, 14 and 16.

The near zone at the tissue surface 18 is at least one cell layer in thickness, and preferably several cell layers in thickness. In practice, it may range from about 100 microns to about 500 microns.

Thus, the positive margin 27 may be defined as a situation where the tissue surface 18, or the near zone at the tissue surface 18, contains at least one cancerous cell.

FIG. 1a further illustrates a clean margin at a location 17, where the tissue surface 18, or the near zone at the tissue surface 18, contains no cancerous cells, and thus has a clean margin 24.

Figure 1B:
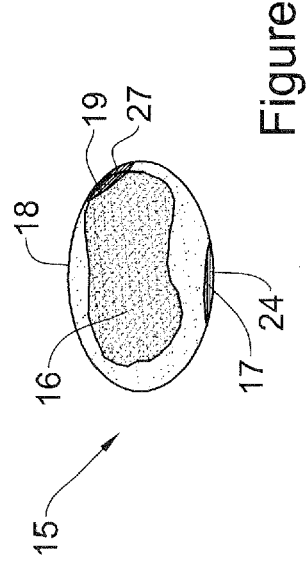

FIG. 1b illustrates another example of the positive margin 27, this time at the location 17. The positive margin of FIG. 1b, however, is due to a shoot 29, which stems from the second tissue type 16 and which reaches to the surface 18.

Figure 1C:
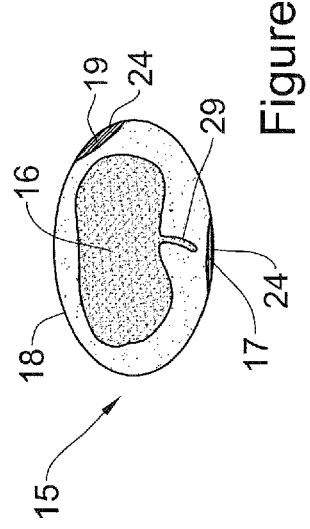
Figure 1D:
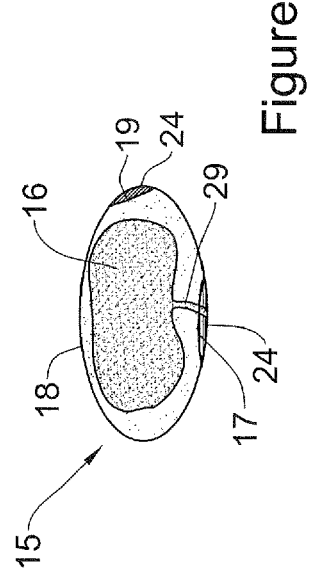

By contrast, FIGS. 1c and 1d illustrate examples of tissue portions 15 that have been excised with clean margins 24, at all locations.

Figure 1E:
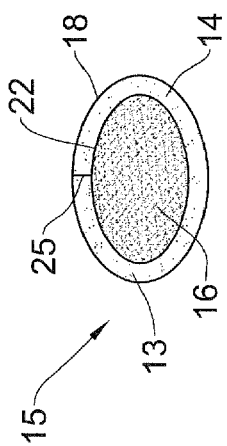

FIG. 1e illustrates a model for clean margin assessment, showing the second, cancerous tissue type 16 and a layer of a tissue 13, surrounding it. The tissue 13 may be a healthy tissue, but may be partly cancerous or otherwise abnormal. The aim in characterizing the tissue surface 18 is to determine the type of the tissue 13 at various locations along the surface 18. Additionally, when the tissue surface 18 is characterized as the clean margin 24, a depth 25 to an interface 22 with the second tissue type 16, may be defined. While a sufficient depth may be realized when the depth 25 is only 1 cell layer in thickness, or about 40 microns, it is generally desired that the depth 25 be between about 0.1 and 10 mm.

It will be appreciated that other dimensions for the depth 25 of the clean margin may be desired and may depend on the size and type of the cancerous tumor, forming the second tissue type 16.

During a surgical operation, for the removal of a cancerous tumor, in a breast for example, it is important to ensure that the incision is made through a healthy tissue, so that all the cancerous tissue is completely contained within the healthy tissue that is being removed. Thus, the indicated need is to remove a tissue portion 15 as shown in FIG. 1e, such that:

i. the cut is made through the first tissue type 14 of healthy tissue, so as to completely contain the second tissue type 16 within;

ii. the depth 25 of the clean margin 24 of the first tissue type 14 is sufficient.

Figure 1F:
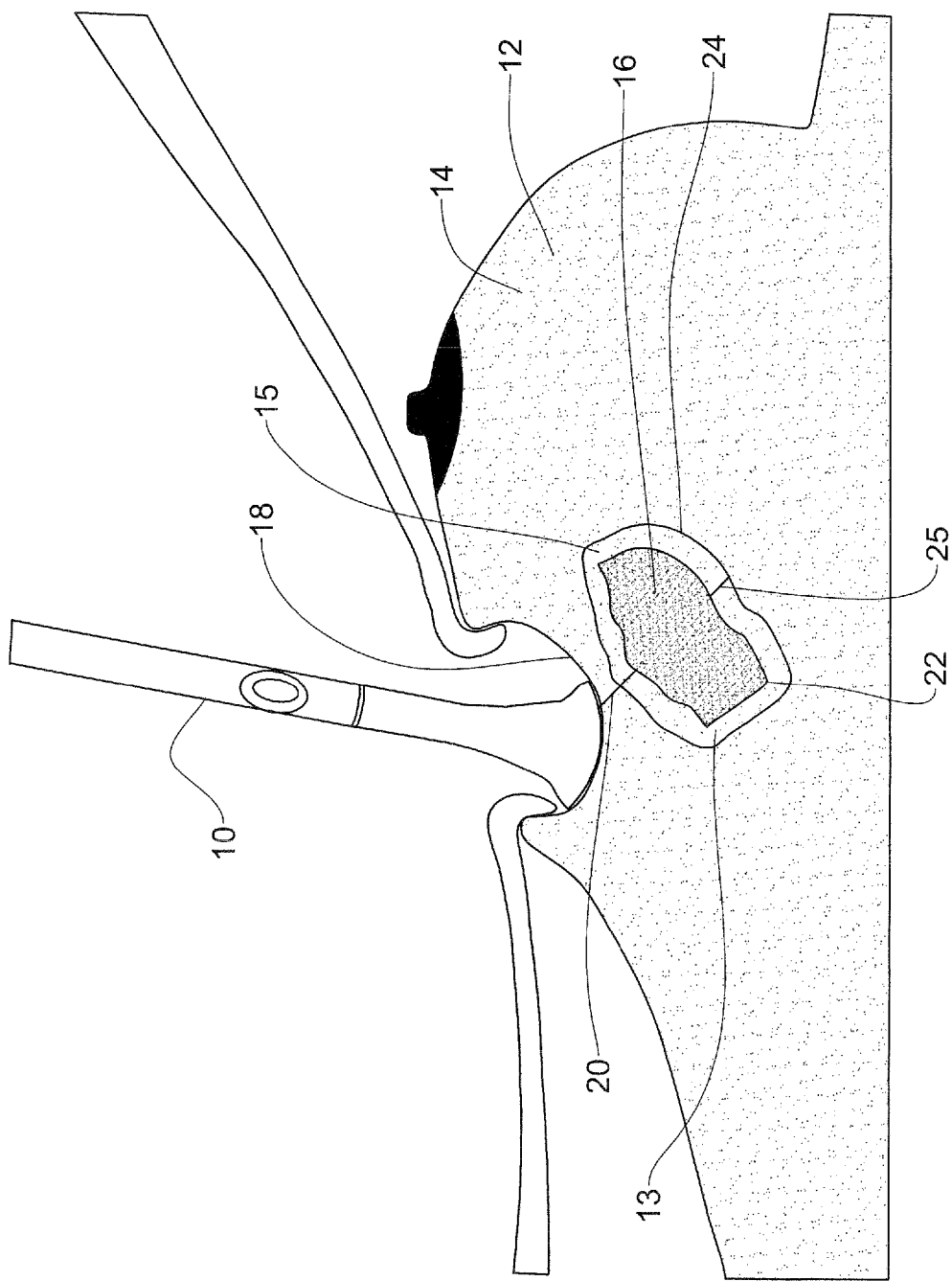

In accordance with the present invention, as illustrated by FIG. 1f, this indicated need is fulfilled by the hand-held, integrated tool 10 for clean-margin assessment, by:

i. a first sensor for characterizing the near zone volume of the tissue surface 18, to ensure that it is of the first tissue type 14 of healthy tissue; and ii. a second sensor for measuring the depth 25 of the clean margin 24, to verify that there is sufficient depth between the tissue surface 18 and the interface 22, which bounds the second tissue type 16.

It is important to note that either sensor alone would be insufficient for the task, since it would not give sufficient information about both the character of the near zone volume of the tissue surface and the depth of the clean margin. The prior art for example, includes methods for determining the depth of the margin but lacks the ability to characterize the tissue of which the margin is formed, so as to ensure that the margin which is measured is clean. It is by this aspect, of both characterizing the tissue of the margin and measuring its depth, that the present invention overcomes the shortcomings of prior art configurations.

FIG. 1f further illustrates the application of the hand-held, integrated tool 10 for clean-margin assessment, to a tissue 12. The tissue 12 includes the healthy tissue, which forms the first tissue type 14. Additionally, the tissue 12 includes the cancerous or otherwise abnormal tissue, which forms the second tissue type 16, enclosed within the first tissue type 14.

In the example of FIG. 1f, the integrated tool 10 determines that a distance 20 between the tissue surface 18 and the interface 22, which bounds the second tissue type 16, is about twice as much as the desired depth 25 of the clean margin 24. In that case, a surgeon may decide to approach the second tissue type 16 further, in order to keep the size of the portion for removal minimal.

It will be appreciated that the integrated tool 10 may be further used to characterize additional tissue types and determine the distances between their interfaces. The various tissue types may include bone tissue, fat tissue, muscle tissue, cancerous tissue, or blood clot tissue.

Referring further to the drawings, FIGS. 2a-2c schematically illustrate an isometric view, a proximal view, with respect to the tissue 12, and a cross-sectional view of the integrated tool 10 for clean-margin assessment, in accordance with a first embodiment of the present invention.

The integrated tool 10 has a proximal end 30 and a distal end 32, with respect to the surface 18 (FIG. 1). In accordance with the preferred embodiment of the present invention, a tissue-type sensor 33 determines the characteristics of the tissue in the near zone volume of the surface 18, for example, whether fat, muscle, bone, healthy, cancerous, or otherwise abnormal. Additionally, a distance-measuring sensor 38 measures the distance 20 from the surface 18 to the interface 22 with the second tissue type 16.

In accordance with the first embodiment of the present invention, the tissue-type sensor 33 measures the electrical properties of the tissue type 13. By comparing the results with known tissue properties, the characteristic of the tissue type 13 is determined.

For example, the tissue-type sensor 33 may be constructed as a coaxial cable 44, having an inner electrode 34 and an outer electrode 36, which together form the sensor 33. The outer electrode 36 may be grounded.

Further in accordance with the first embodiment of the present invention, the distance-measuring sensor 38 is at least one ultrasound transducer 38.

Preferably, the coaxial cable 44 is located within an overall structure 45. The distance-measuring sensor 38, such as the at least one ultrasound transducer 38 is also mounted on the structure 45, for example, along side the tissue-type sensor 33.

Additionally, the distance-measuring sensor 38 may be formed of at least two ultrasound transducers 38, one operating as a transmitter and the other as a receiver. The advantage there is that the instrumentation dead time is shorter.

Furthermore, the distance-measuring sensor 38 may be formed as an array of ultrasound transducers 38, for providing steering and focusing capabilities, as known.

Signals from the tissue-type sensor 33 and the distance-measuring sensor 38 are transferred for analysis through a cable 46 to a computerized system 95, described hereinbelow in conjunction with FIG. 6.

Preferably, the inner electrode 34 has a diameter 40 of between about 0.2 and 1.5 mm, and the outer electrode 36 has an inner diameter 42 of between about 3.0 and 10.0 mm, and is about 0.5 mm thick. Additionally, the outer electrode 36 is covered with an insulating sheath 49 made of an insulating material, for example, Teflon. It will be appreciated that other dimensions, which may be larger or smaller, may similarly be used. The sensors 38 and 33 may be encased in a filler material 39, for example epoxy, which may be formed as a plug that fits into the structure 45, for example, as shown in FIG. 2c.

Preferably, the ultrasound transducer 38 operates at a frequency range of between about 0.5 MHz and about 40 MHz. It has an accuracy of about 3 mm, when operating at the lower range of 0.5 MHz, and an accuracy of about 40 micron, when operating at the higher range of 40 MHz.

The integrated tool 10 may further include a position-tracking device 50, for example, the miniBIRD® 500 or the miniBIRD® 800, which are miniaturized magnetic tracking systems having six degrees of freedom and using sensors, which are merely 5 mm wide, produced by Ascension Technology Corporation, P.O. Box 527 Burlington, Vt. 05402, USA. They are described in http://www.ascension-tech.com/products/minibird.php, downloaded on Mar. 15, 2005. The position-tracking device 50 may provide the coordinates of the ultrasound measurements, thus enabling a three-dimensional image reconstruction of the ultrasound.

Figure 3:
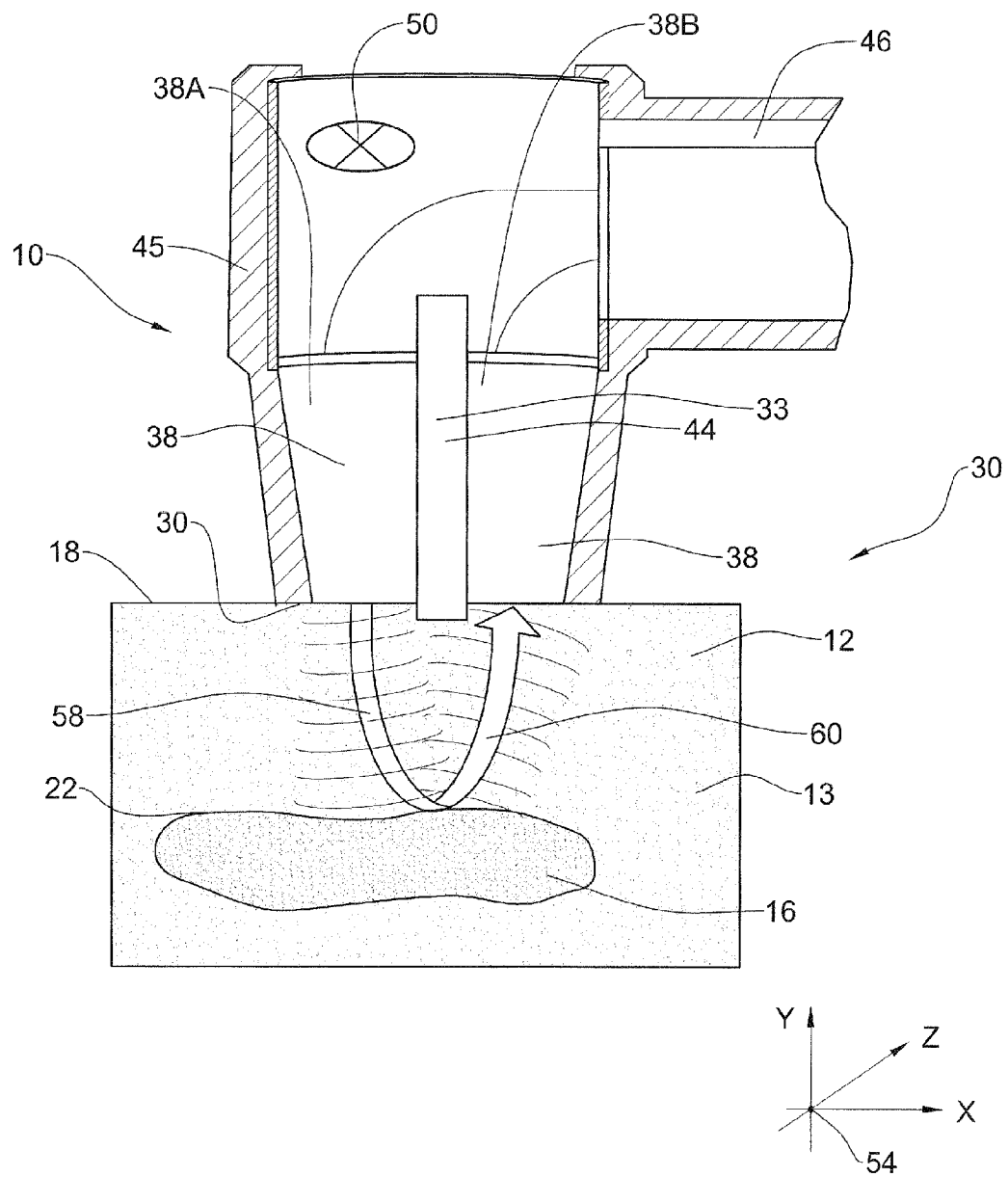
FIG. 3 schematically illustrates an ultrasound distance-measuring sensor of the integrated tool for clean-margin assessment, in accordance with the present invention.

Referring further to the drawings, FIG. 3 schematically illustrates the ultrasound distance-measuring sensor 38 of the integrated tool 10, in operation, in accordance with the present invention.

For operation, the proximal end 30 of the integrated tool 10 is brought proximally to the tissue surface 18, of the tissue 12, so as to make contact or near contact with it. The tissue 12 includes the first tissue type 14 of healthy tissue, preferably at the outer portion thereof, and the second tissue type 16 of abnormal tissue, enclosed by the first tissue type 14 of healthy tissue, with tissue 13, which is suspicious as possibly containing cancerous or otherwise abnormal tissue, surrounding the second tissue type 16. Preferably, tissue 16 is bounded by the interface 22.

Preferably, at least two ultrasound transducers 38 are used, 38A and 38B, wherein the transducer 38A is a transmitter for transmitting an ultrasound wave 58, and the transducer 38B is the receiver, for receiving an ultrasound echo 60, from the interface 22 within the tissue 12. In this manner, instrumentation dead time is reduced.

Preferably, the ultrasound sensor 38 is preset for a focal distance of about 5 mm, which is the desired depth 25 of the clean margin 24, thus providing the most accurate results for this distance.

FIG. 3 further illustrates the structure 45 of the coaxial cable 44 and the tissue-type sensor 33. Additionally, the position-tracking device 50 is shown. When correlated with a tissue coordinate system 54, illustrated hereinbelow, in conjunction with FIG. 6, it may be used together with the ultrasound sensor 38, to provide a three-dimensional image of the tissue 12 and the abnormal tissue type 16 within.

The cable 46 carries the measurements to the computerized system 95, described hereinbelow in conjunction with FIG. 6.

Referring further to the drawings, FIGS. 4a-4d further illustrate the operational manner of the integrated tool 10 for clean-margin assessment, in accordance with the present invention.

Generally, to localize the tumor within the breast, a radiologist may place a guide wire under x-ray or ultrasound guidance, so that the proximal tip of the guide wire, with respect to the tissue, is in the tumor. Alternatively, an imaging modality alone, for example, mammography, CT, ultrasound, or another imaging modality may be used to locate the tumor. The patient is then transported to the operating room, where the surgeon uses the guide wire, or the image, or palpation to locate the tumor in the breast and to excise a portion of tissue including the cancerous portion and a layer of healthy tissue surrounding the cancerous portion. The process of inserting a guide wire is termed, pre-procedure.

In accordance with the present invention, two methods are possible, without pre-procedure, as illustrated in FIGS. 4a-4c, and with pre-procedure, as illustrated in FIG. 4d.

Thus, FIGS. 4a-4c schematically illustrate the use of the integrated tool 10 when no guide wire is used.

As seen in FIG. 4a, the integrated tool 10 may be used on the tissue surface 18, during the removal of the portion 15, to verify that the cutting proceeds as planned. At this stage, the near zone volume of the surface 18 should detected by the tissue type sensor 33 to be of the first tissue type 14 of healthy tissue, and the interface 22 with the second tissue type 16 should be detected at the desired depth 25. Corrections can be made in real time.

As seen in FIG. 4b, the integrated tool 10 may be used on the tissue surface 18, after the removal of the portion 15, to verify that the all the cancerous tissue has been eliminated. At this stage, the near zone volume of the surface 18 should detected by the tissue type sensor 33 to be of the first tissue type 14 of healthy tissue, and no interface 22 and no second tissue type 16 should be detected. As seen in FIG. 4b, where a portion 72 of the second tissue type 16 remained, the integrated tool 10 will identify it both by the character of the near zone volume of the tissue surface 18 around the portion 72, and by the presence of the interface 22, in back of the second tissue type 16, indicating that two types of tissue remained.

As seen in FIG. 4c, the integrated tool 10 may be used on the tissue surface 18, of the removed portion 15, after removal. This, to verify that the all the cancerous tissue is surrounded by the clean margin 24 of the first tissue type 14 of healthy tissue, and of sufficient depth 25. At this stage, the near zone volume of the surface 18 should be of the first tissue type 14, and the interface 22 should be detected at the desired depth 25.

Additionally, as seen in FIG. 4c, where there is no clean margin, as shown by a surface 74, the integrated tool 10 will identify it both by the character of the near zone volume of the tissue surface 18 at the surface 74, and by the absence of the interface 22, around the desired depth 25.

FIGS. 4d schematically illustrates the use of the integrated tool 10 with a guide wire 78 that has been inserted during pre-procedure, with the help of x-ray or another imaging modality. This procedure often applies to non-palpable tumors, which are difficult to detect.

Preferably, the distance-measuring sensor 38 is an ultrasound transducer, and the guide wire 78 is visible by the ultrasound. Additionally, a guide-wire transducer 82 may be mounted on the tip 80, for sending signals that may be received by the distance-measuring sensor 38. Thus, the distance-measuring sensor 38 may estimate the distance to the tip 80, hence the distance to the second tissue type 16.

The guide wire transducer 82 may be, for example, a micro-electromechanical system (MEMS) ultrasound transducer, with a typical size of about 100 μm in diameter. Furthermore, the distance-measuring sensor 38 may include three transducers, for calculating the exact position of the guide wire transducer 82, by triangulation. It will be appreciated that in the calculation of the distance between the guide wire transducer 82 and the distance-measuring sensor 38, it is assumed that the sound velocity in cancerous tissue and in healthy tissue is about the same.

Alternatively, the sensor 82 at the tip 80 of the guide wire 78 may be a magnetic positioning device, coupled with an RF transmitter, for transmitting its position, via RF signals, which may be received by an RF receiver on the integrated tool 10.

When the portion 15 has been removed, FIGS. 4b and 4c apply, as before.

Figure 5A:
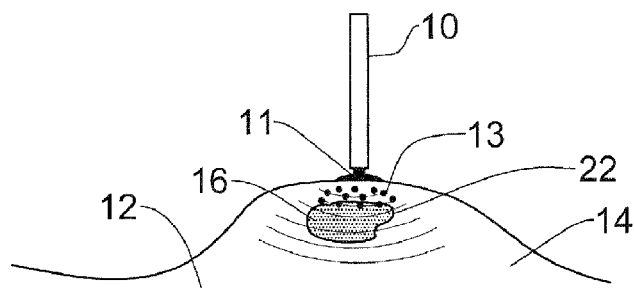
FIGS. 5a-5c further illustrate the operational manner of the integrated tool for clean-margin assessment, in accordance with the present invention.
Figure 5B:
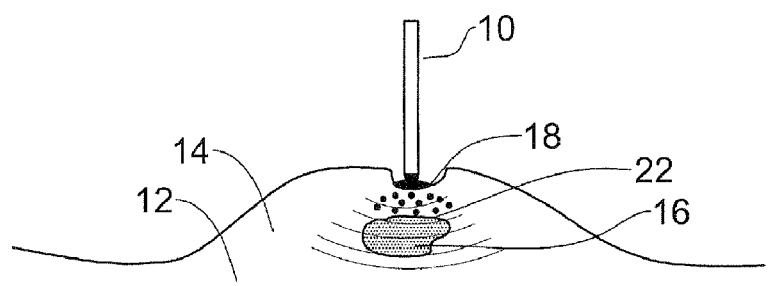
Figure 5C:
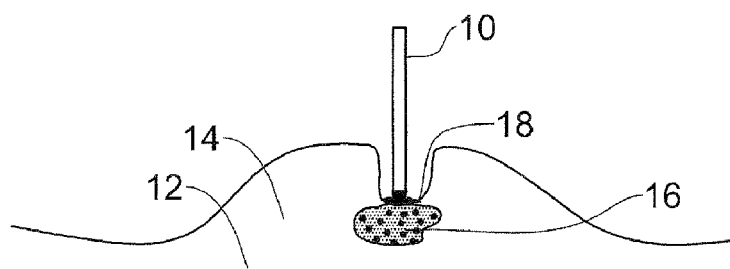

Referring further to the drawings, FIGS. 5a-5c further illustrate the operational manner of the integrated tool 10 for clean-margin assessment, in accordance with the present invention.

As seen in FIG. 5a, as a first step, the integrated tool 10 is applied to an external surface 11, such as a skin, forming the surface 18, prior to cutting and prior to the removal of the portion 15 (FIG. 1). Alternatively, the surface 18 may be a lumen. The tissue-type sensor 33 will probably detect that the surface 18 is of the first tissue type 14 of healthy tissue, and the distance-measuring sensor 38 will detect the interface 22 with the second tissue type 16 at some depth.

As seen in FIG. 5b, when the incision begins, for the removal of the portion 15 (FIG. 1), the integrated tool 10 is applied to the tissue surface 18, now the tissue surface 18, to verify that the cutting proceeds as planned. At this stage, the tissue-type sensor 33 will detect that the near zone volume of the tissue surface 18 is of the first tissue type 14 of healthy tissue, and the distance-measuring sensor 38 will detect the interface 22 with the second tissue type 16 at some depth, approaching the desired depth 25 of the clean margin 24. Corrections and adjustments can be made in real time.

As seen in FIG. 5c, if cutting went too far, the tissue-type sensor 33 will detect that the near zone volume of the tissue surface 18 is of the second tissue type 16 of abnormal tissue, and the distance-measuring sensor 38 will not be able to provide useful information, as no clean margin exists.

Figure 6:
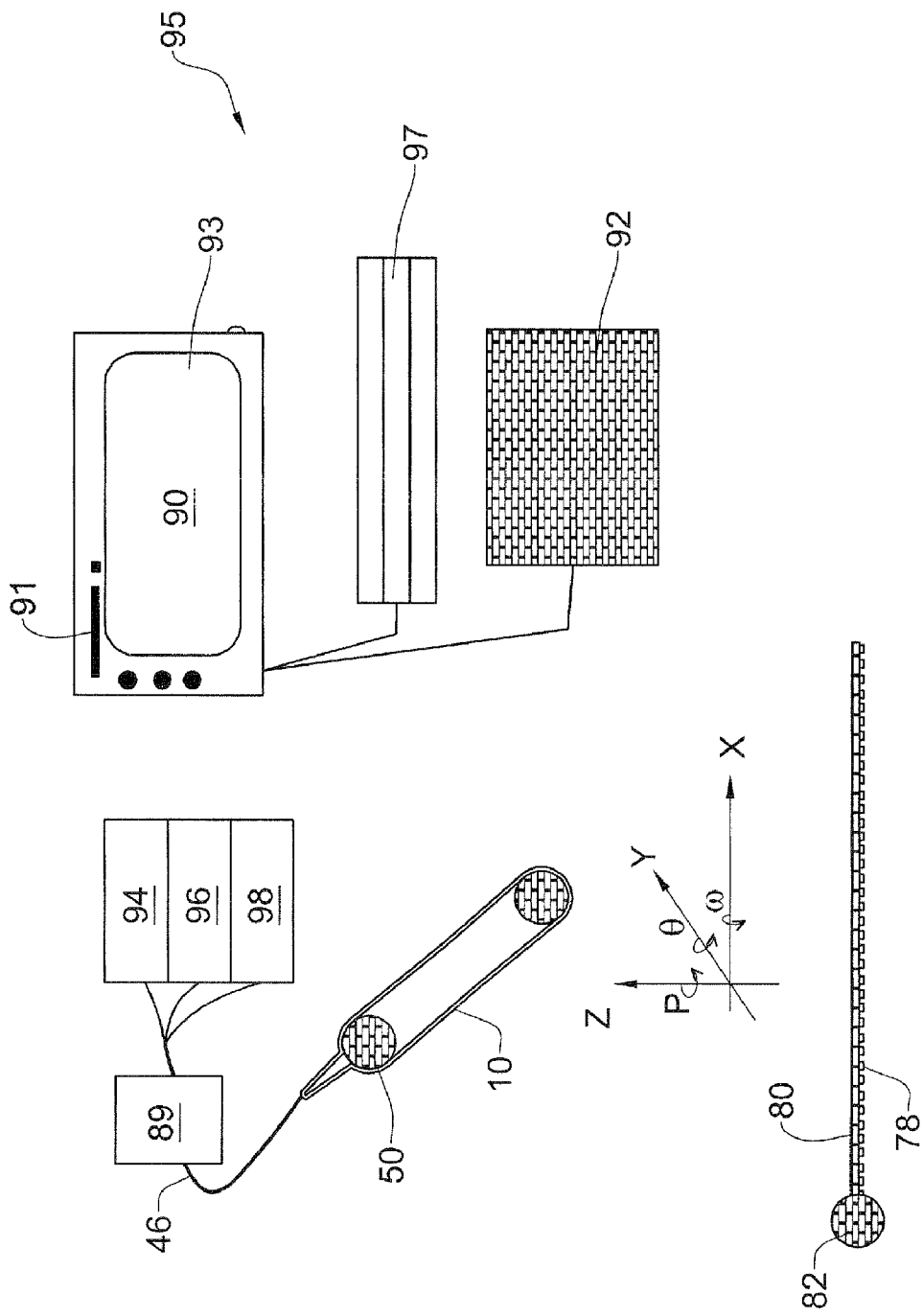
FIG. 6 schematically illustrates an overall system for clean-margin assessment, in accordance with the present invention.

Referring further to the drawings, FIG. 6 schematically illustrates an overall computerized system 95, for clean-margin assessment, in accordance with the present invention.

System 95 includes the integrated tool 10, having the structure 45, on which the tissue-type sensor 33 and the distance-measuring sensor 38 are mounted. Preferably, both sensors are located at the proximal end 30, with respect to the tissue. Additionally, the integrated tool 10 may include the position-tracking device 50, for providing its coordinates with respect to the frame of reference 54, which defines a six-degree coordinate system, of x, y, z, and the rotational angles around them, $\omega$, $\theta$, and $\rho$.

Data from the integrated tool 10 is carried to appropriate analyzers, preferably associated with a computer 90 for analysis. It will be appreciated that the computer 90 may be a personal computer, a laptop, a palmtop, a microcomputer, or another computer, as known.

For example, where the tissue-type sensor 33 is an electrical properties sensor, constructed essentially as the coaxial cable 44 (FIGS. 2a-2c), an electrical properties sensing module 94 includes, for example, an impedance analyzing external unit, such as Agilent 4396A, and a test fixture 89 connected via a coaxial cable to the impedance analyzing external unit.

Similarly, the distance-measuring sensor 38, such as the ultrasound transducer 38 is associated with an ultrasound signal generator and analyzer 96. The position-tracking device 50 may be associated with an analyzer 98. The sensors may be battery operated or associated with power supply units.

The computer 90 which receives the data from the analyzers, preferably includes a user interface, for example, a keyboard 97, or knobs, and may further include storage systems, such as a read and write drive 91, a USB port 93, and a display screen 92.

It will be appreciated that where a different tissue-type sensor 33 is used, the unit 94 type will complement that sensor 33. For example, where sensor 33 is an optical sensor, the unit 94 will be an optical analyzer. Similarly, where a different distance measuring sensor 38 is used, the unit 96 will complement that sensor 38.

Information from the distance-measuring sensor 38 together with that of the position-tracking device 50 may be used for reconstructing a three-dimensional image of the tissue, by the computer 90. Additionally, the three-dimensional image may be displayed on the screen 92.

The system 95 may further include a guide wire 78. At the proximal end 80, the guide wire may include a sensor 82, which may be an ultrasound transducer or a magnetic positioning device, coupled with a transmitter, for transmitting the positioning of the proximal tip, when inserted in the tissue, as taught hereinabove, in conjunction with FIG. 4d. Preferably, the sensor 82 is wireless, and operates via external interrogation, for example, from the distance-measuring sensor 38, or on battery.

Referring further to the drawings, FIGS. 7a-7d schematically illustrate the integrated tool 10, which further includes a retractable knife 106, in accordance with a preferred embodiment of the present invention.

Figure 7A:
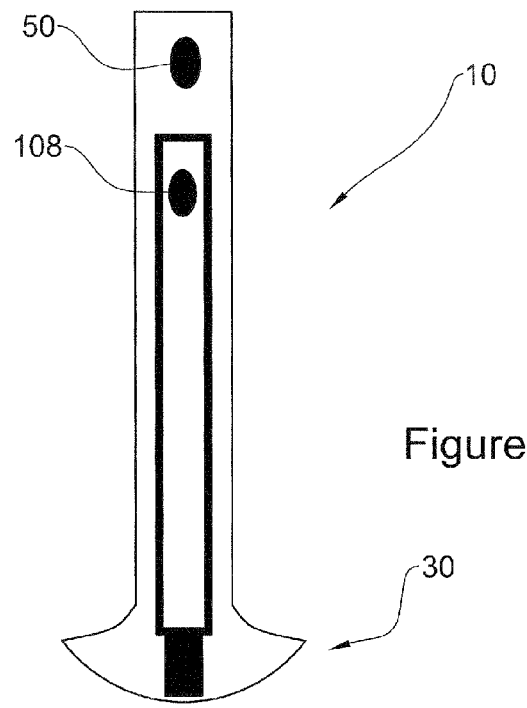
FIGS. 7a-7d schematically illustrate the integrated tool for clean-margin assessment, which further includes a retractable knife, in accordance with a preferred embodiment of the present invention.

As seen in FIG. 7a, the knife is retracted, and the tool is used as described hereinabove.

Figure 7B:
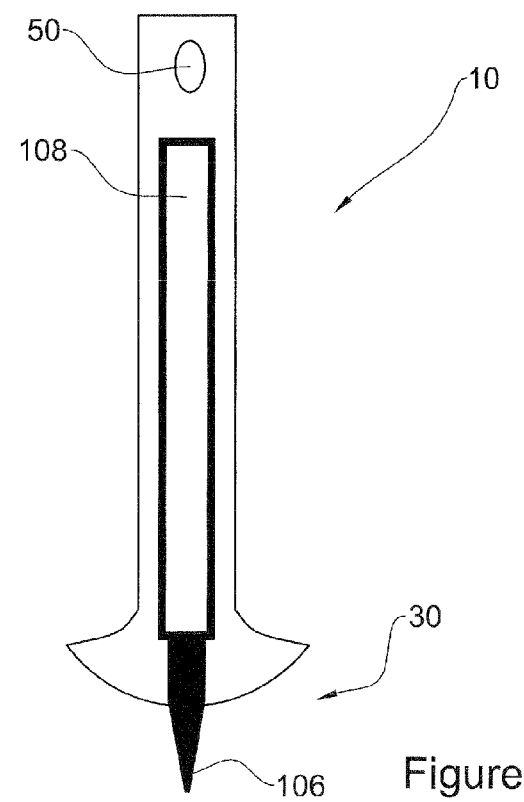

As seen in FIG. 7b, the knife is deployed, and the tool is used for removing the portion 15.

Thus the surgeon may use the integrated tool 10 both for measuring and characterizing the clean margin and for removing the portion 15.

Figure 7C:
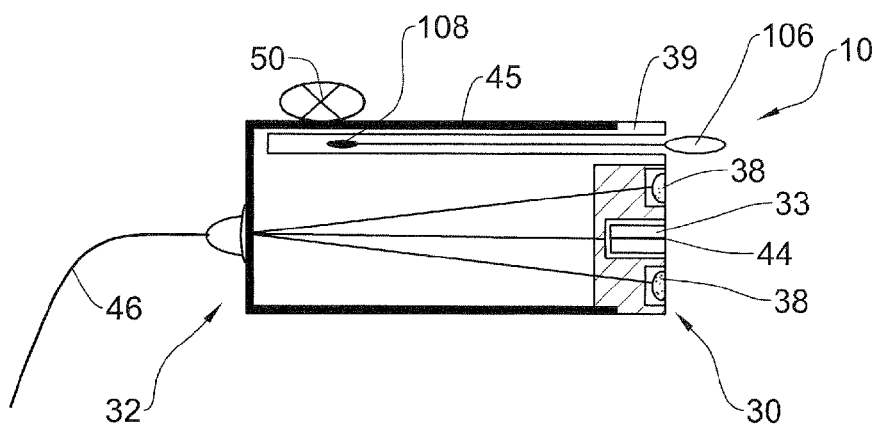
Figure 7D:
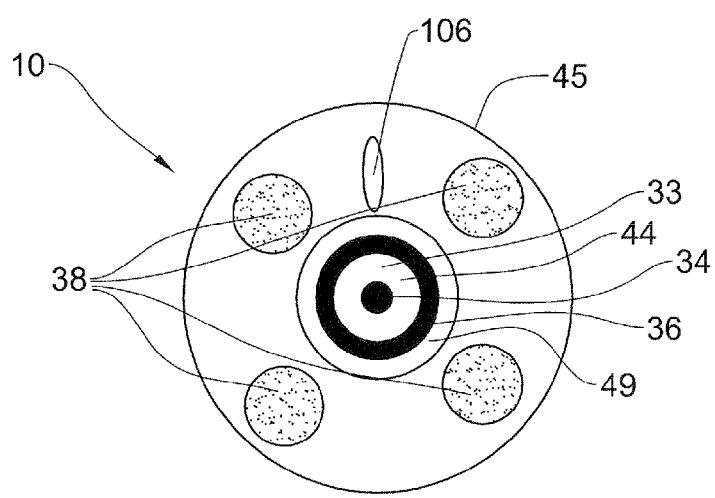

FIG. 7c illustrates the proximal view of the integrated tool 10, in accordance with the present embodiment, while FIG. 7d provides a cross-sectional view.

Retraction and deployment are controlled by a knob 108.

The knife 106 may be a cold knife, a diathermal knife, or another knife, as known.

Referring further to the drawings, FIGS. 8a-8b schematically illustrate the integrated tool 10, operative with a frame 100 for fixing the soft tissue 12, in accordance with a preferred embodiment of the present invention.

The frame 100 has a support plate 101 and a compression plate 102. The compression plate 102 defines an opening 104, through which the integrated tool 10 may be inserted.

In accordance with the present invention various sensors may be used for the tissue-type sensor 33, for characterizing the near zone volume of the tissue surface 18 in contact with the integrated tool 10. These are illustrated below, in conjunction with FIGS. 9a-12b.

Referring further to the drawings, FIGS. 9a and 9b schematically illustrate the integrated tool 10, wherein the tissue-type sensor 33 is formed as an RF or MW horn antenna 37, mounted on the structure 45, in accordance with still another embodiment of the present invention.

The RF or MW horn antenna 37 is associated with an RF/MW transmission line or wave guide 31, while unit 94 (FIG. 6) is an RF/MW generation, collection and analysis unit.

The present embodiment relies on RF microwave characterization by the generation of propagating radiation in the RF microwave region of the electromagnetic spectrum, towards the tissue, and measuring its reflection. The radiation is usually transmitted and received by an antenna, for example the horn antenna 37. The tissue characterization is done by analyzing the amplitude and phase difference between the original waves to the reflected wave.

Figure 10B:
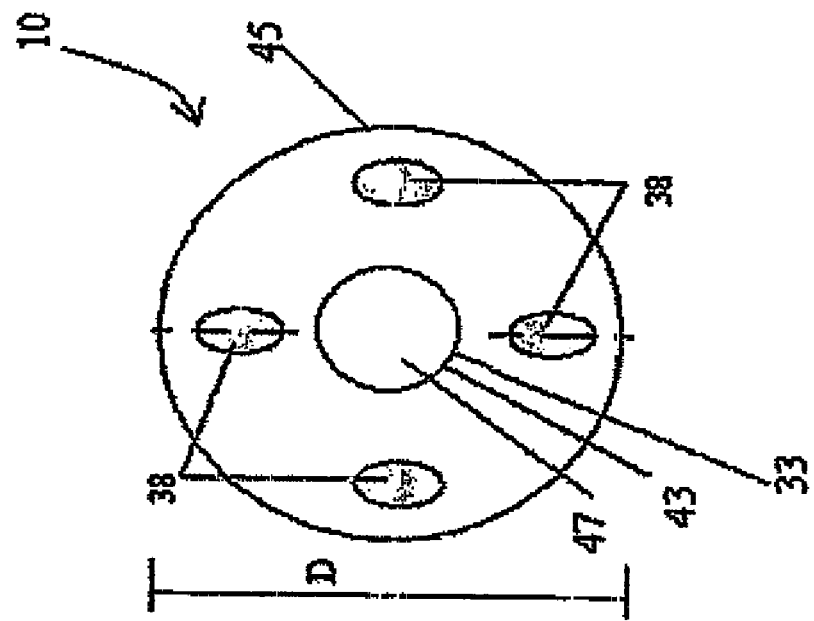
FIGS. 10a and 10b schematically illustrate the integrated tool for clean-margin assessment, wherein the tissue-type sensor is formed as an optical sensor, in accordance with yet another embodiment of the present invention.
Figure 10A:
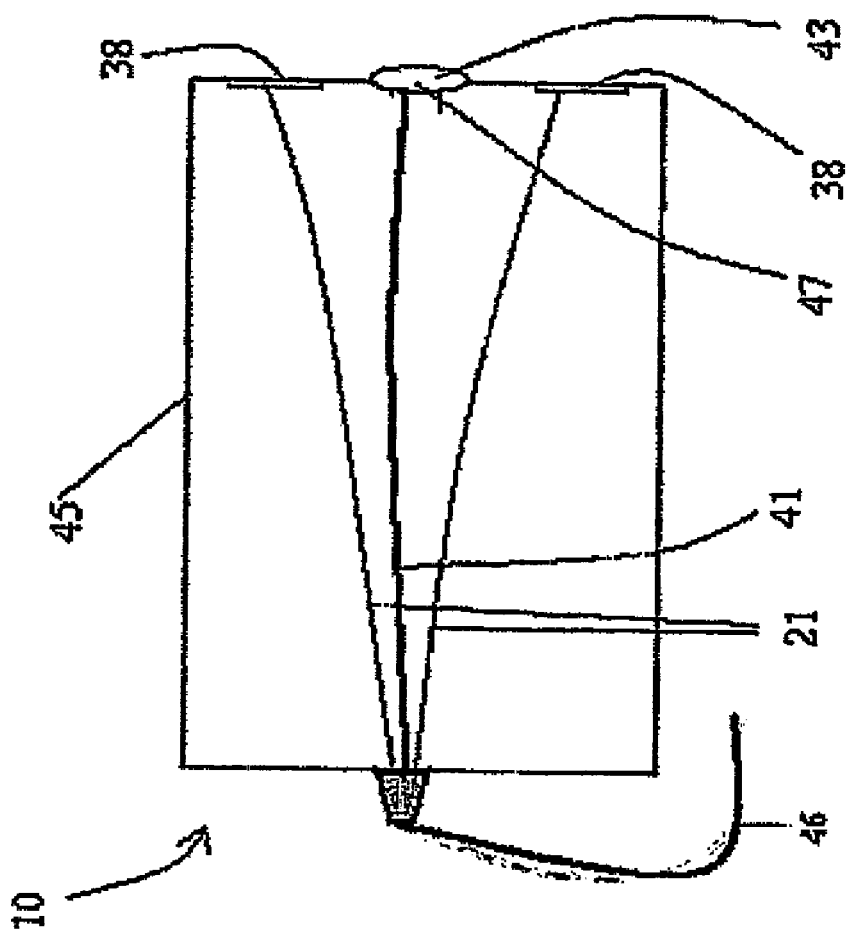

Referring further to the drawings, FIGS. 10a and 10b schematically illustrate the integrated tool 10, wherein the tissue-type sensor 33 is formed as an optical sensor 47, mounted on the structure 45, in accordance with yet another embodiment of the present invention.

An optical signal is generated in an external unit, such as unit 94 (FIG. 6) and transmitted via an optical fiber 41 to the tissue. The reflection of the light is then received in a dedicated module inside the optical unit. The optical energy is usually transmitted to and from the tissue via a lens 43.

The details of optical signal generation, receiving and analyzing depend on the specific optical method that is chosen. For example, for reflection spectroscopy, tissue characterization relies on measuring the relative amplitude and phase of the reflected light versus the generated light. An example for the reflection spectroscopy method is described in commonly owned U.S. patent application Ser. No. 10/298,196, whose disclosure is incorporated herein by reference. It will be appreciated that other methods may be used, as known.

Alternatively, auto florescence may be used, for measuring emitted radiation, from the tissue, at different a wavelength than that originally transmitted. The emitted radiation occurs in response to excitation by impinging radiation, and may be used for tissue characterization, for example, as used by Xillix Technologies Corp., #100-13775 Commerce Parkway, Richmond, British Columbia, Canada V6V 2V4, Telephone: 604-278-5000, and described in http://www.xillix.com/index_home.cfm. It will be appreciated that other methods may be used, as known.

Figures 11A, 11B:
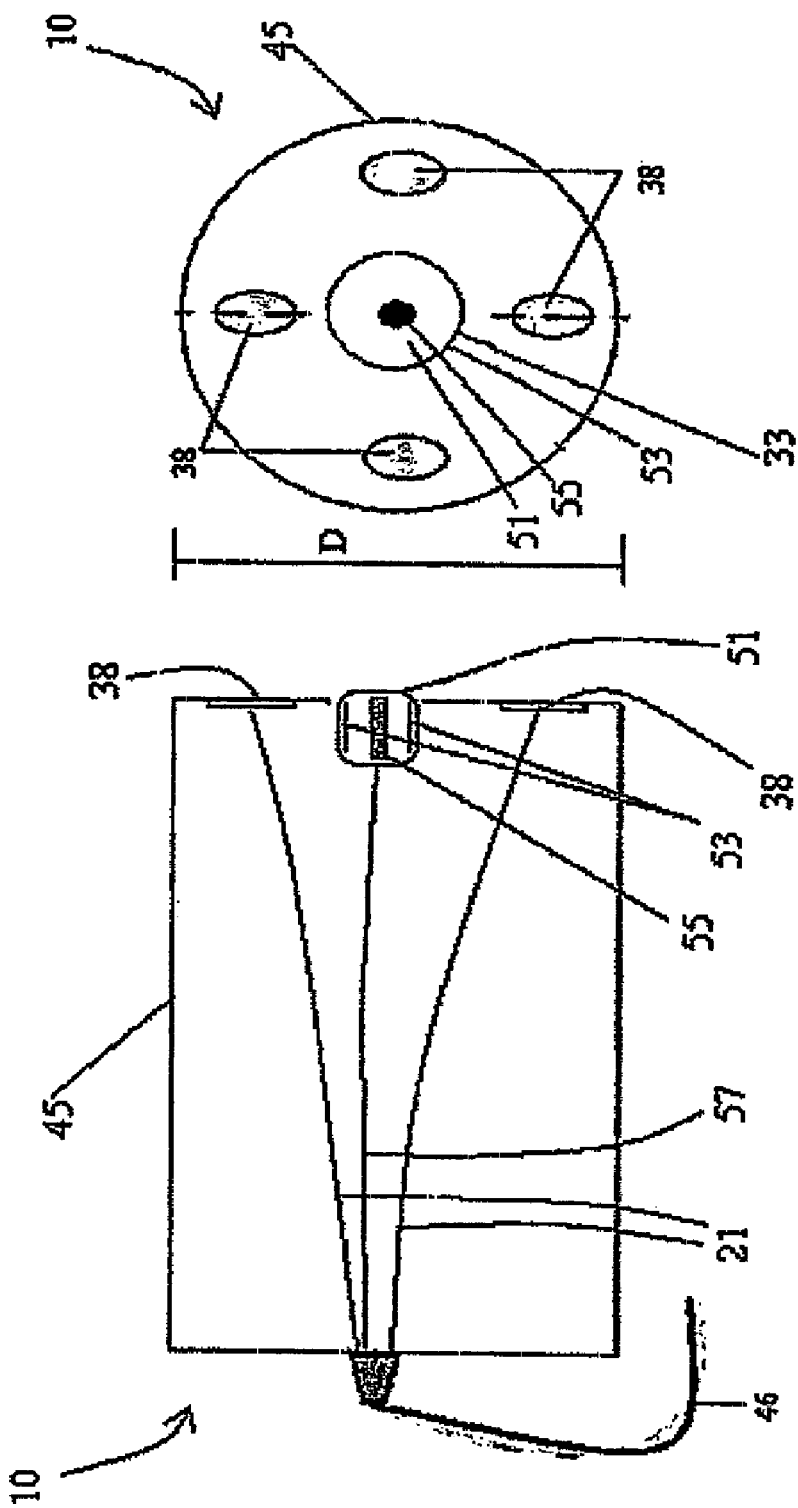
FIGS. 11a and 11b schematically illustrate the integrated tool for clean-margin assessment, wherein the tissue-type sensor is formed as an MRI sensor, in accordance with yet another embodiment of the present invention.

Referring further to the drawings, FIGS. 11a and 11b schematically illustrate the integrated tool for clean-margin assessment, wherein the tissue-type sensor 33 is formed as an MRI sensor 51, in accordance with yet another embodiment of the present invention.

The MRI sensor 51 has a permanent magnet 55, enclosed in an RF coil 53, for example, as taught in commonly owned US Patent Application 2005/0021019 to Hashimshony et al., entitled "Method and apparatus for examining substance, particularly tissue, to characterize its type," whose disclosure is incorporated herein by reference, and in U.S. Pat. No. 5,572,132, to Pulyer, et al., entitled, "MRI probe for external imaging," whose disclosure is incorporated herein by reference.

In accordance with the present invention various sensors may be used for the distance-measuring sensor 38, as illustrated below, in conjunction with FIG. 13.

It will be appreciated that many other tissue characterization sensors may be used, as known. These may include a sensor for tissue electromagnetic properties, a dielectric sensor, an impedance sensor, a sensor for optical fluorescence spectroscopy, a sensor for optical reflectance spectroscopy, an MRI sensor, a temperature sensor, and infrared thermography sensor, or another tissue-characterization sensor, as known.

Figure 12A:
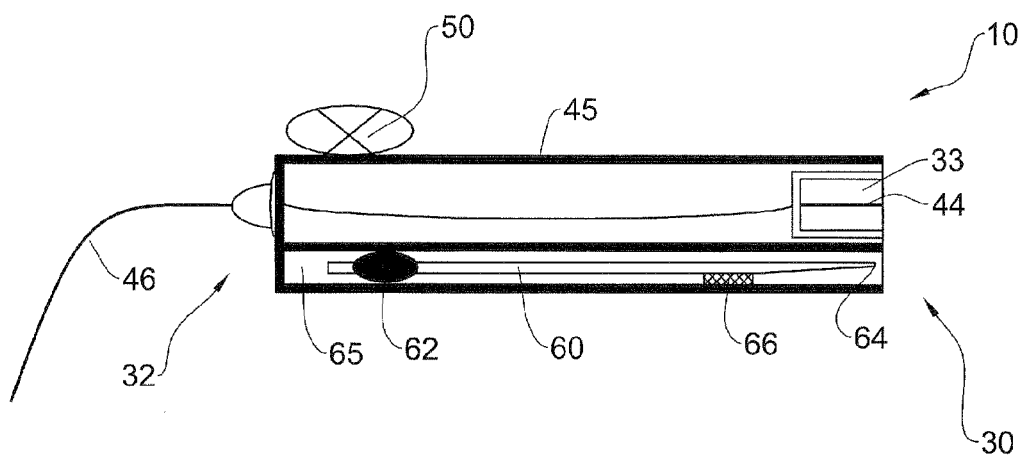
FIGS. 12a and 12b schematically illustrate the integrated tool for clean-margin assessment, wherein the distance-measuring sensor is formed as a strain gauge, in accordance with still another embodiment of the present invention.
Figure 12B:
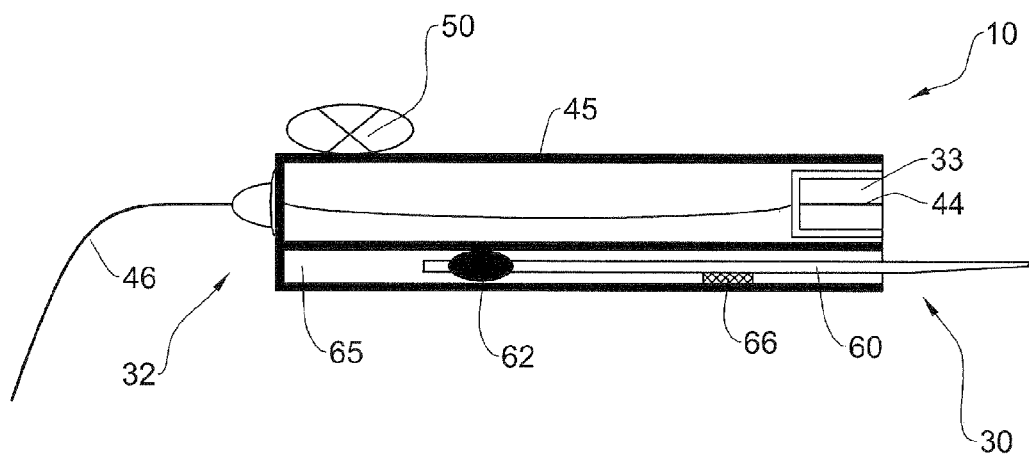

Referring further to the drawings, FIGS. 12a and 12b schematically illustrate the integrated tool 10, wherein the distance-measuring sensor 38 is formed as a strain gauge 66, in accordance with still another embodiment of the present invention.

The present embodiment utilizes the approach of U.S. Pat. No. 6,546,787 to Schiller et al., whose disclosure is incorporated herein by reference, and which provides an apparatus and method for detecting a distance from a tissue edge to a malignant tissue, enclosed therein, i.e., a margin. The apparatus comprises a needle having a strain gage, mounted on one of the needles walls. Strain signals are collected as the needle is moved through the tissue. The needle is inserted at different points to allow data collection from different points within the tissue. The data is sent together with its spatial coordinates to a computerized system, which provides an image of the structure of the examined tissue.

As seen in FIGS. 12a and 12b, the structure 45 of the integrated tool 10 may include a lumen 65, wherein a needle 60 may be retracted and deployed, via a knob 62. The needle has a sharp edge 64, for penetrating the tissue. The strain gauge 66 senses the tissue resistance to the penetration, and provides data of resistance as a function of needle penetration depth. These measurements may be performed at various locations along the tissue surface 18.

Figure 13A:
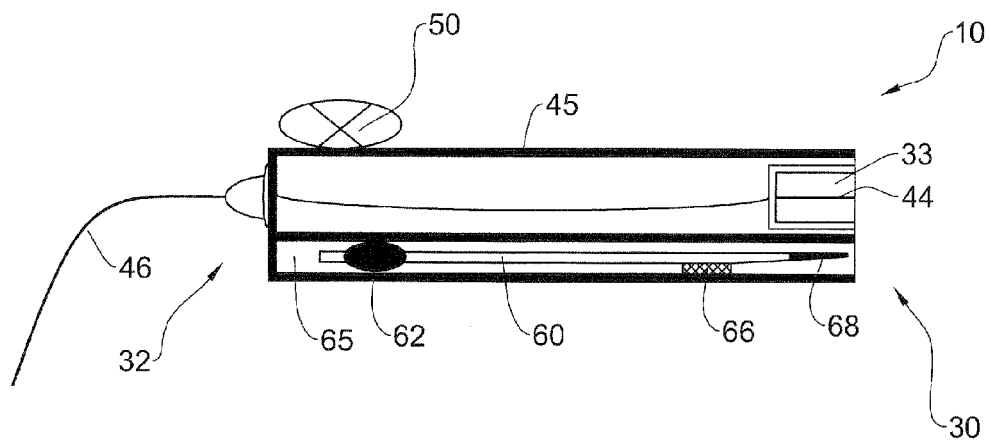
FIGS. 13a and 13b schematically illustrate the integrated tool for clean-margin assessment, wherein the distance-measuring sensor is formed as a pressure sensor, in accordance with still another embodiment of the present invention.
Figure 13B:
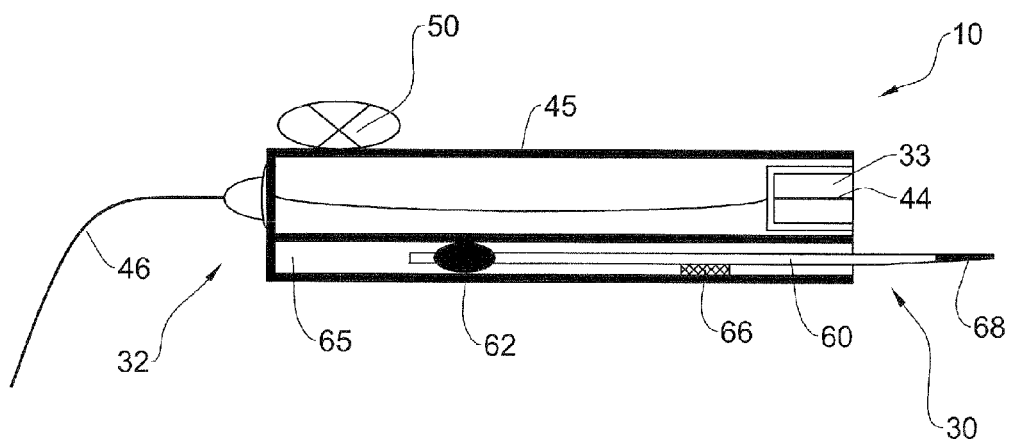

Referring further to the drawings, FIGS. 13a and 13b schematically illustrate the integrated tool 10, wherein the distance-measuring sensor 38 is formed as a pressure sensor 68, at the needle's tip, in accordance with yet another embodiment of the present invention.

Again, the structure 45 of the integrated tool 10 may include the lumen 65, wherein the needle 60 may be retracted and deployed, via the knob 62. The pressure sensor 68 senses the tissue resistance to the penetration, and provides data of resistance as a function of needle penetration depth. These measurements may be performed at various locations along the tissue surface 18.

It will be appreciated that a non-invasive imager may be used for the distance-measuring sensor 38, for example, an MRI sensor.

Accordingly, the integrated tool 10 may be formed, for example, with the tissue-type sensor 33 being an optical sensor, and the distance-measuring sensor 38 being a on-invasive imager, such as an MRI sensor.

Figure 14A:
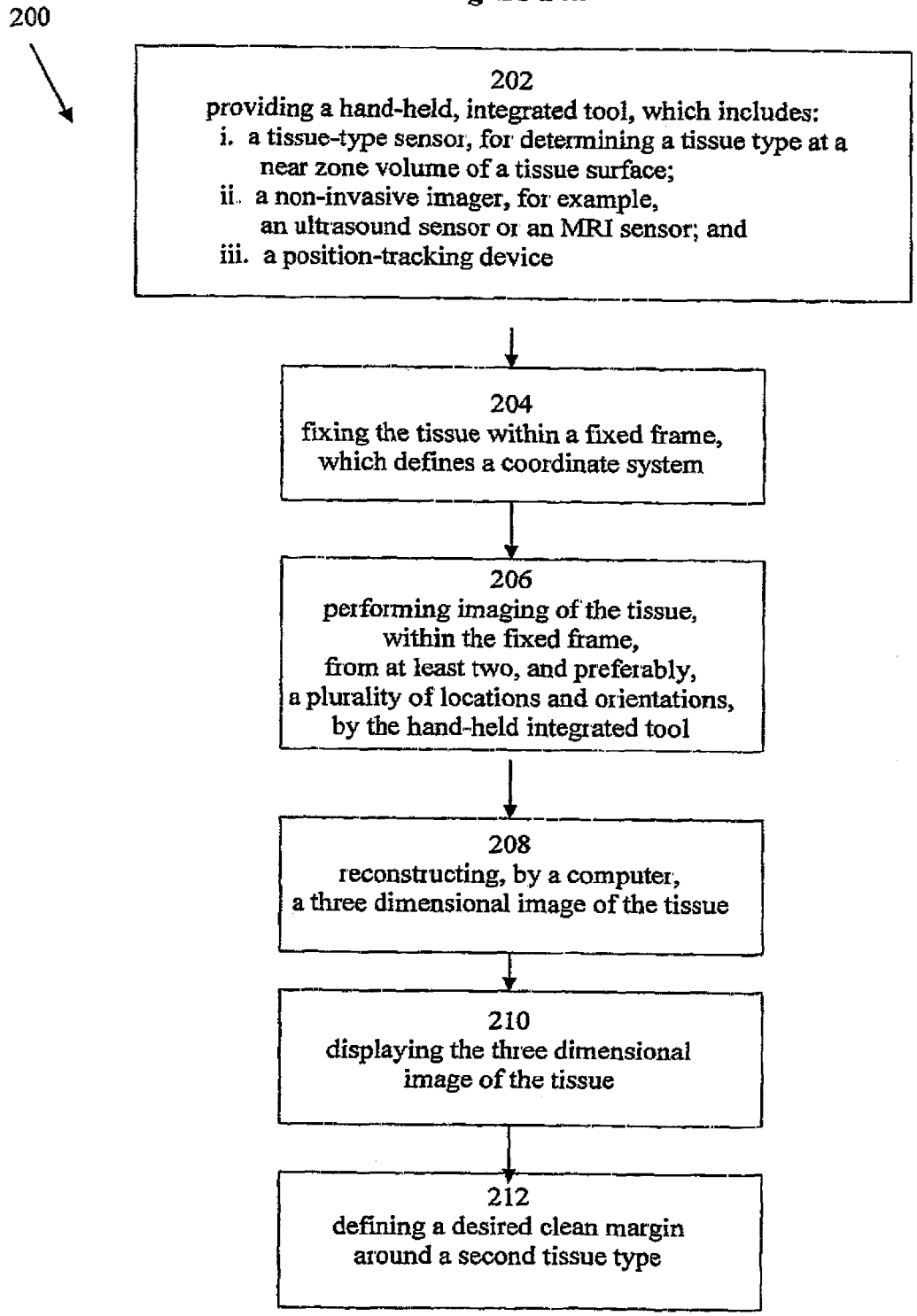
FIGS. 14a 14b illustrate, in flowchart forms, surgical methods of tumor removal, using the integrated tool for clean-margin assessment, in accordance with embodiments of the present invention.
Figure 14B:
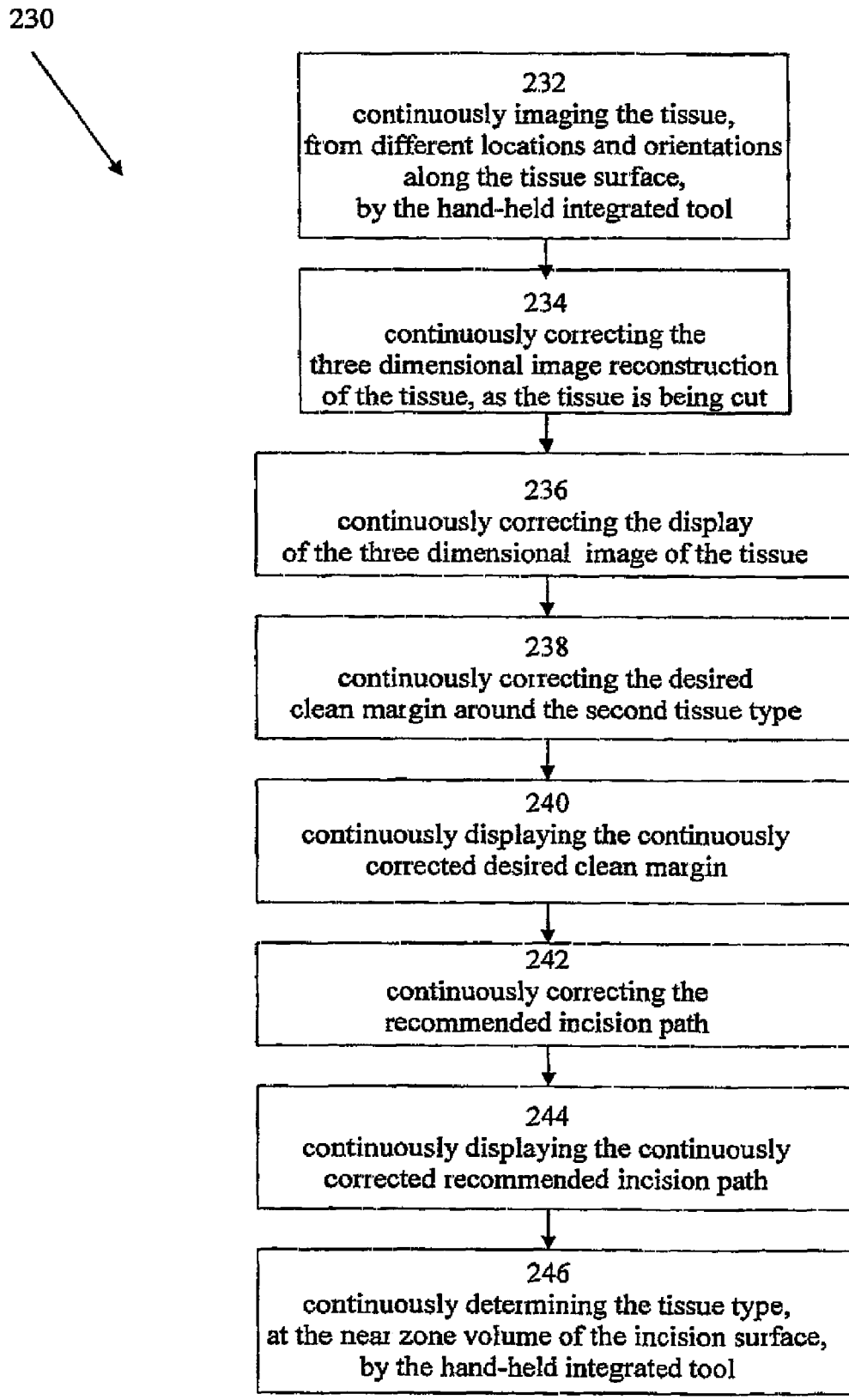

Referring further to the drawings, FIGS. 14a and 14b illustrate, in flowchart forms, surgical methods of tumor removal, using the integrated tool 10, in accordance with embodiments of the present invention, As illustrated in FIG. 14a, a method 200 provides a computer-guided surgery, as follows:

in a box 202: providing the hand-held, integrated tool 10, which includes:
1. the tissue-type sensor 33, for determining a tissue type at a near zone volume of a tissue surface;
2. the non-invasive imager 38, for example, an ultrasound sensor, or an MRI sensor; and
3. the position tracking device 50.

in a box 204: fixing the tissue within a fixed frame, which defines a coordinate system, preferably of six-degrees, x, y, z, and the rotational angles around them, $\omega$, $\theta$, and $\rho$.

in a box 206: imaging the tissue, within the fixed frame, from at least two, and preferably, a plurality of locations and orientations, by the hand-held, integrated tool 10.

in a box 208: reconstructing, by a computer, a three dimensional image of the tissue.

in a box 210: displaying the three dimensional image of the tissue.

in a box 212: defining a desired clean margin around a second tissue type.

in a box 214: displaying the desired clean margin.

in a box 216: calculating a recommended incision path.

in a box 218: displaying the recommended incision path.

in a box 220: providing an incision instrument.

in a box 222: cutting along the recommended incision path.

in a box 224: determining the tissue type at the near zone volume of the tissue surface, by the hand-held, integrated tool 10.

As illustrated in FIG. 14b, a method 230 further provides continuous correction to the method 200, as follows:

in a box 232: continuously imaging the tissue, from different locations and orientations along the tissue surface, by the hand-held, integrated tool 10.

in a box 234: continuously correcting the three dimensional image reconstruction of the tissue, as the tissue is being cut.

in a box 236: continuously correcting the display of the three dimensional image of the tissue.

in a box 238: continuously correcting the desired clean margin around the second tissue type.

in a box 240: continuously displaying the continuously corrected desired clean margin.

in a box 242: continuously correcting the recommended incision path.

in a box 244: continuously displaying the continuously corrected recommended incision path.

in a box 246 continuously determining the tissue type, at the near zone volume of the incision surface, by the hand-held, integrated tool 10.

Preferably, the knife is integrated with the tool, as taught in conjunction with FIGS. 7a-7d.

Figure 15A:
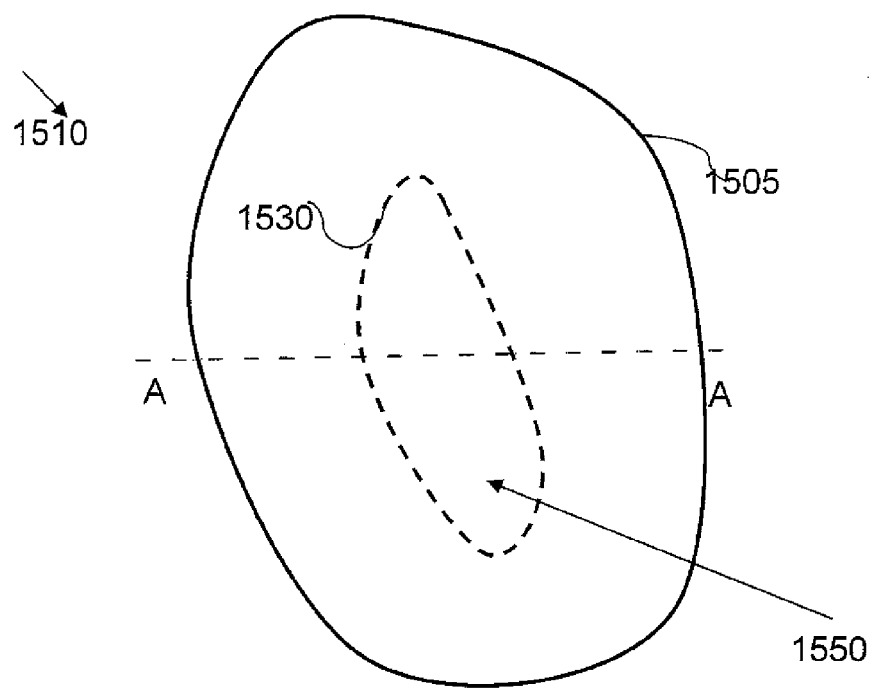
FIGS. 15a to 15c illustrate the principles of a clean margin technique in accordance with the present invention, where
Figure 15B:
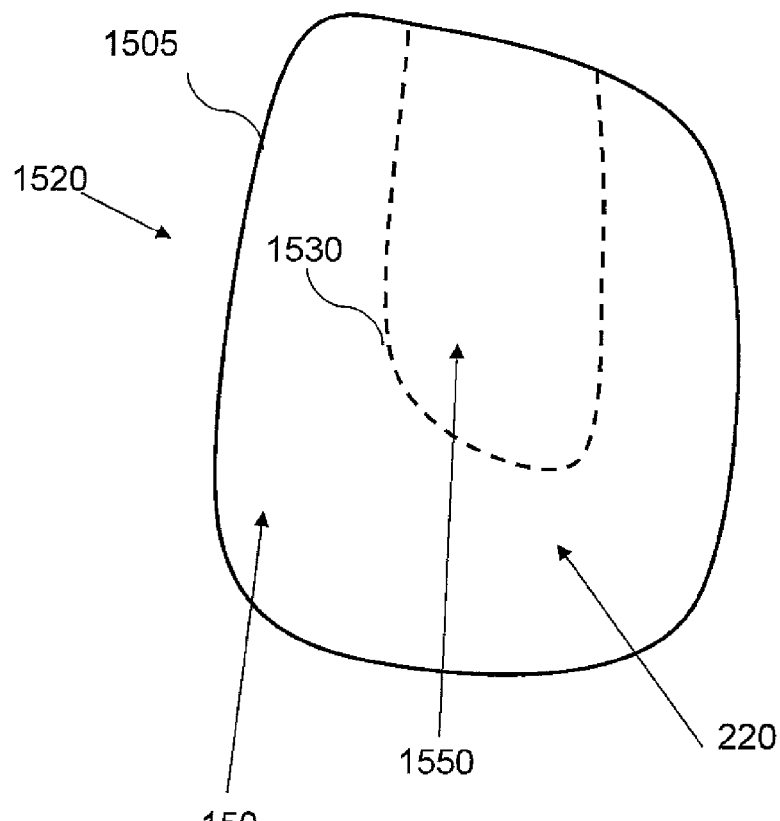
Figure 15C:
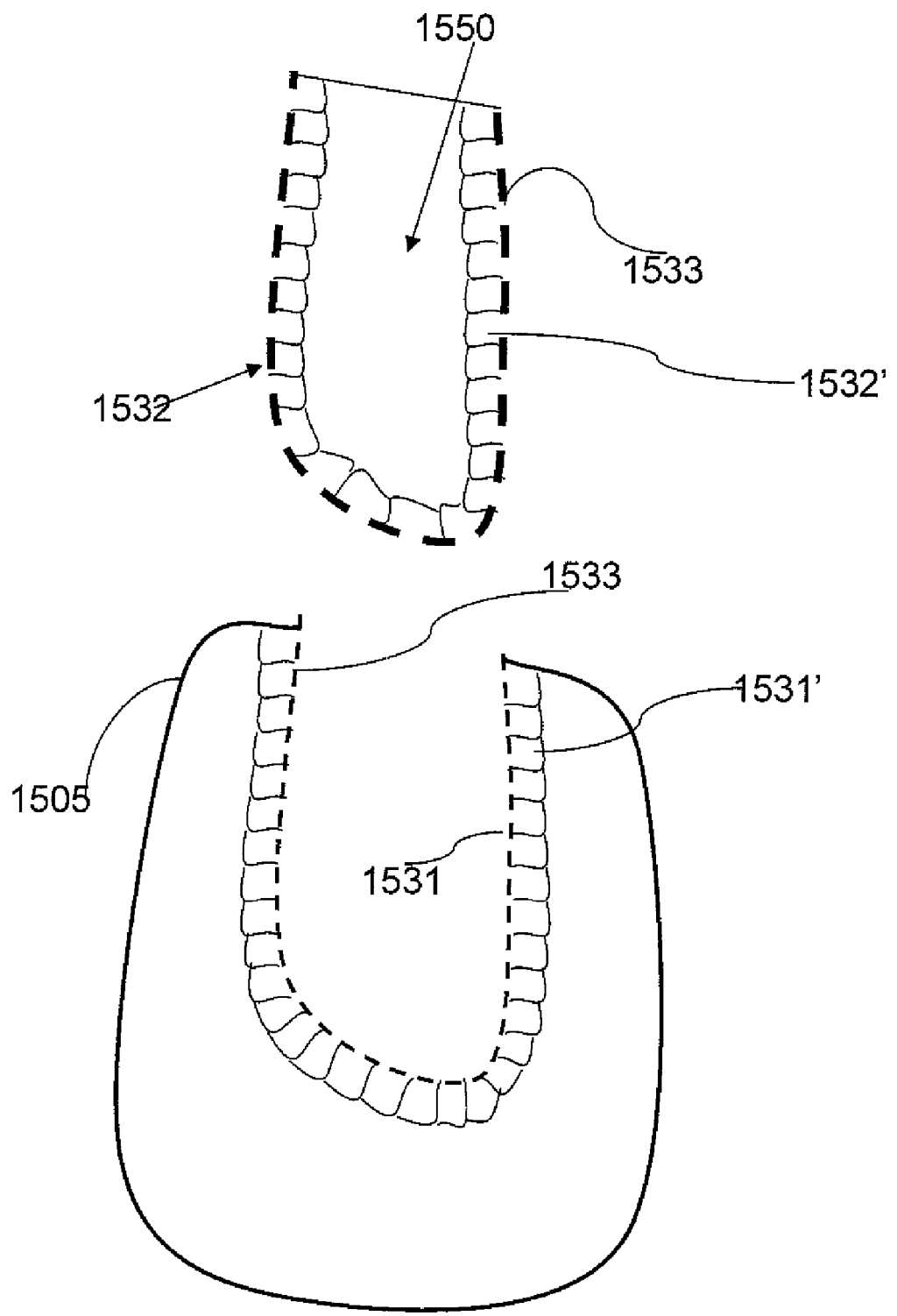

Referring further to the drawings, FIGS. 15a-15c schematically illustrate the principles of providing a clean margin, in accordance with the present invention.

FIGS. 15a and 15b illustrate a top view 1510 and a cross sectional view 1520, respectively, of a tissue part 1505 and an incision surface contour 1530 within tissue part 1505. The incision surface 1530 surrounds a tissue region (portion) 1550 which may be removed from the tissue part 1505 during a surgical process for achieving a clean margin (i.e. obtaining the incision surface 1530 or the near zone at the incision surface 1530 with no abnormal tissue cells). In other words, identification of a clean margin within the surrounding or periphery of the tissue portion 1550, which has abnormal tissue cells signifies that tissue 1550 can be removed and no removal of additional surrounding tissues is required.

The tissue portion 1550 may include for example a lesion, or a tumor, or any other abnormal tissue. The lesion, or the tumor, or the abnormal tissue, is to be fully and completely removed, with a clean margin surrounding it. The tissue part 1505 and the tissue portion 1550 therein may be a skin portion, a body lumen portion, an organ, an anatomical feature, some portion of intra-corporeal tissue, or a combination theirs. The tissue 1550 may be removed from a body, either completely or partially. The incision surface 1530 may be an incision surface contouring an organ, or an anatomical feature. According to some embodiments of the present invention the incision surface 1530 may be defined by a diagnostic modality, or by a surgeon.

As shown in FIG. 15c, the excision of tissue portion 1550 from the tissue 1505 (along the incision contour 1530) forms two separated surfaces (illustrated by a dashed curve 1533). A first surface, e.g. surface 1531, includes newly exposed surface segments 1531' of the tissue 1505. The surface 1531 may include the inner surface, the intact tissue related surface, the cavity surface. A second surface, e.g. surface 1532, includes newly exposed surface segments 1532' of the tissue portion 1550. The surface 1532 may also be termed as the outer surface, the removed tissue related surface, the excised tissue related surface, the lump surface.

A process for achieving a clean margin includes a characterization process followed by an incision/additional tissue removal process. According to some embodiments of the present invention, during the characterization process the inner surface 1531 and/or the outer surface 1532 are characterized to determine whether a tissue portion such as the tissue portion 1550 has been excised with the clean margins. The incision/additional tissue removal process follows the characterization process. The characterization and incision/additional tissue removal cycle may be continued until for example the characterized tissue surface contains no cancerous cells, and thus has a clean margin. Alternatively, the incision/additional tissue removal process following the characterization process may include removal for example of a specific organ, or anatomical feature, for example without additional characterization cycles. According to some embodiments of the present invention, during or following the incision/additional tissue removal process an additional characterization process and/or corrections for the clean margins may be preformed.

Figure 16B:
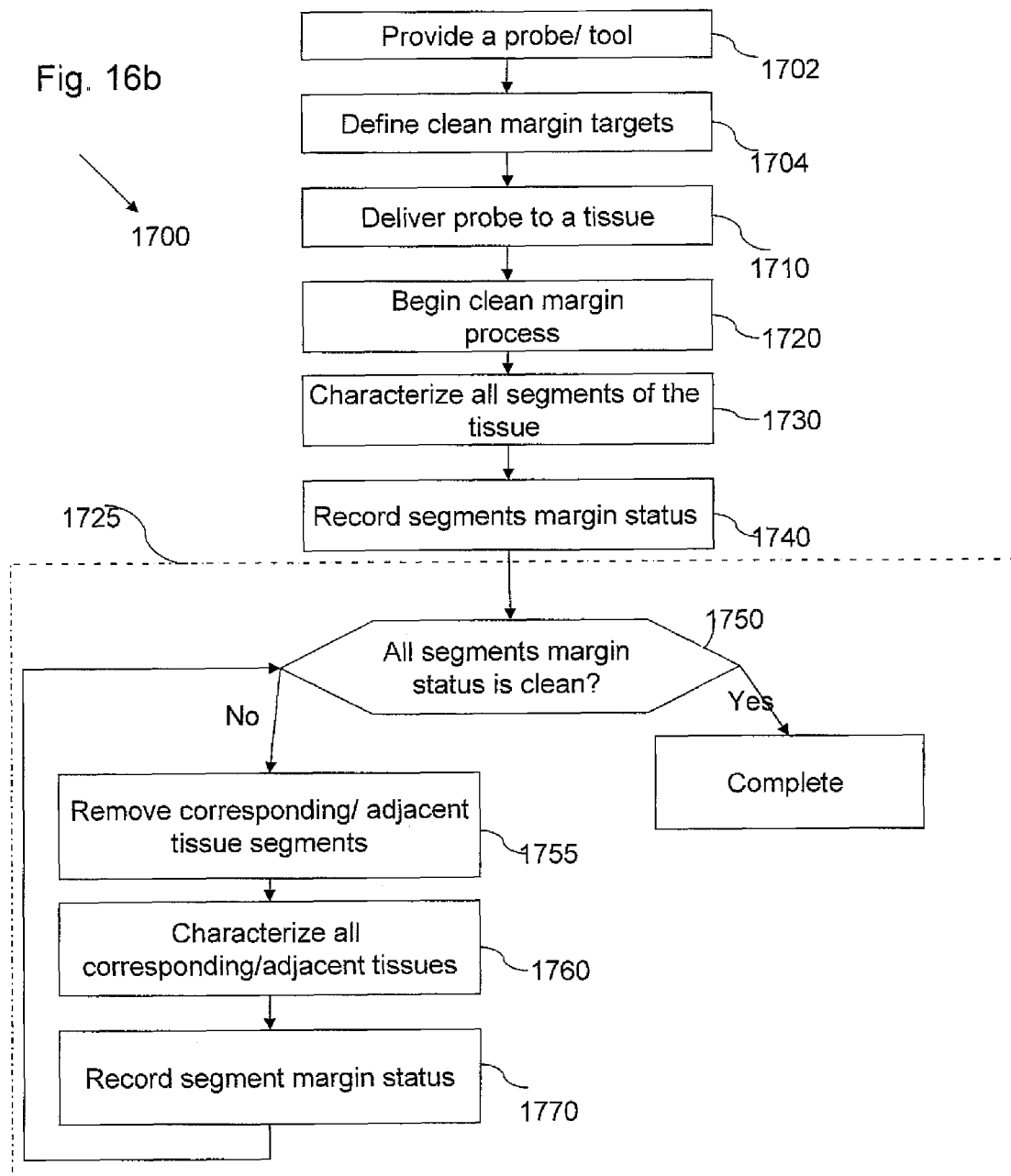

Reference is now made to FIGS. 16a and 16b illustrating flowcharts 1600 and 1700 of a method for providing a clean margin of healthy tissue around a malignant tumor or abnormal tissue, in accordance with some embodiments of the present invention. As illustrated in flowchart 1600, a medical probe or tool for characterizing a tissue is provided (step 1602). The probe includes one or more tissue-type sensors, such as the above-described tissue-type sensor 33, or an array of sensors for determining the characteristics of a tissue surface, such as tissue surfaces 1531 or 1532, for example in the near zone volume of the tissue surface. According to some embodiments of the present invention, the probe is configured as the above-described integrated tool 10 for clean-margin assessment. According to some other embodiments of the present invention, the probe is configured similar to that described in U.S. application Ser. No. 10/891,750 and/or in U.S. Pat. No. 6,813,515, each of which are assigned to the common assignee of the present application and each of which is hereby incorporated by reference. It should be understood that the probe may have other configurations and other sets of components.

The clean margin status targets are defined (step 1604). To this end, the clean margin status targets may be selected from, but is not limited to: no abnormal tissue at the characterized tissue surface; no abnormal tissue up to a given depth from the characterized tissue surface, such as a 1 mm or 2 mm depth, or up to 20 mm depth. The probe is delivered to a tissue (step 1610), such as the tissue 1505 shown in FIGS. 15a-15c. The clean margin process achievement begins (step 1620), and the process enters a control cycle (steps 1625). A first segment is characterized (step 1630), for example at a 'near zone' tissue surface (e.g. 0-20 mm), to determine, preferably in real-time, based upon the characterization of the tissue at the present segment, whether the first segment is characterized as having a clean margin (step 1640). The first segment may be for example one of the tissue segments 1531' or 1532'. A characterization result/data or a margin status of each examined segment may be recorded in a memory utility located for example in the probe, and may be further displayed on the computer screen. The margin status of each examined segment may be further transmitted to the external computer or to an external memory device such as a removable memory e.g. a DiskonKey or other small and portable memory device. The margin status of each segment which was recorded or saved may be used for example for additional procedures such as pathology procedure related to the examined tissue e.g. tissue 1505 or to a different body lumen or anatomical feature of a patient.

According to some embodiments of the present invention, a session data may be saved for example in a computerized system, such as the above described computerized system 95, for further analysis. The session data may include for example, a reconstructed three-dimensional image of a tissue portion (e.g. an examined tissue surface such as the tissue portion 1550), the coordinates and margin status of all segments in the tissue portion. The session data may be exported and transmitted to an external device/computer or to an external memory device such as a removable memory e.g. a DiskonKey or other small and portable memory device. The session data which was recorded or saved may be used, for example, in additional procedures, such as pathology procedures, related to the examined tissue, additional surgical or diagnostic procedures, related to the respective patient.

A segment margin status result may be defined as a positive result or negative result. If positive, e.g. the first segment is characterized as having a clean margin, then the probe is displaced and relocated to the next tissue segment to determine whether all segments of the tissue surface were characterized as having a clean margin (steps 1645, 1680, 1640). The relocation of the probe may be manual, semi-manual or automatic employing for example, a two-dimensional or three-dimensional computer controlled stage, as is known in the art. There may be a computer program which controls the stage and defines the sequence of moving the probe from one location or segment to the next. In cases, where the relocation is manual or semi-manual, the system may provide an operator with specific instructions on how and to whereto move the probe. If all the tissue segments are characterized as having a clean margin, then the achieving clean margin process is completed. If no, the probe is displaced and relocated to the next tissue segment to characterize the next tissue segment (step 1680) and determine whether the next tissue segment has a clean margin or not (step 1640). The next segment may be located, for example adjacent to or in proximity to the previously characterized segment. If the first characterized segment has no clean margin, then a tissue segment adjacent to the first tissue segment is removed from the body (step 1650). The tissue removal may be done using an incision instrument, which may for example be attached to the probe to enable cutting and removing the tissue region while characterizing the respective tissue segment. The removed tissue segment or the surface of the tissue from where the tissue was removed is characterized (step 1660) for determining whether it has a clean margin. If negative, e.g. the removed tissue segment or the surface of the tissue from where the tissue was removed includes a clean margin, then the clean margin assessment process is continued and the process returns to step 1680 for characterizing the next segment. If positive, e.g. the removed tissue segment or the surface of the tissue from where the tissue segment was removed does not include a clean margin, then the process returns to step 1650 and the tissue adjacent to at least the location of the tissue segment at which there was no clean margin is removed from the body.

According to some embodiments of the present invention the output data relating to the margin status of for example all characterized tissue segments may be recorded and transmitted to the computer system and may be displayed on the computer screen. According to some embodiments of the present invention the clean margin process may be performed for providing a clean margin during a procedure for characterizing an anatomical feature. An example of anatomical feature may be a prostate.

FIG. 16b shows flowchart 1700 according to another example of the present invention. A probe or tool for characterizing a tissue is provided (step 1702), the probe/tool may include one or more tissue-type sensors, such as the above described tissue-type sensor 33, for determining the characteristics of a tissue surface, such as tissue surfaces 1531 or 1532, for example in the near zone volume of the tissue surface. The probe may be configured as the above described integrated tool 10 for clean-margin assessment, or may have other configurations and other sets of components.

The clean margin process targets are defined (step 1704). The clean margin process targets may be selected, as for example but is not limited to: no abnormal tissue at the characterized tissue surface; no abnormal tissue up to a given depth from the characterized tissue surface, such as a 1 mm or 2 mm depth, or up to 20 mm depth. The probe is delivered to a tissue (step 1710), such as the tissue 1505, or tissue portion 1550, shown in FIGS. 15a-15c. The clean margin process begins (step 1720). All the segments (1531' and or 1532') of the tissue surface 1531 and or 1532 are characterized (step 1730). The margin status of all segments is reordered (step 1740) or registered for example by a computerized system, such as the computerized system 95 for clean-margin assessment, described hereinabove in conjunction with FIG. 6. The margin status which is based on the defined clean margin targets may be negative, e.g. the segment is characterized as having a clean margin, or positive, e.g. the segment is characterized as not having a clean margin.

According to some embodiments of the present invention the margin status of all segments which was reordered or registered may be used for determining an incision path, for example for decision-making during an operation as to the delimitation of the abnormal tissue e.g. the segments which were characterized as not having a clean margin.

The achieving clean margin process enters a control cycle (steps 1725) which includes the following: Based upon the margin status of each segment, it is determined, preferably in real time, whether all the tissue segments are characterized as having a clean margin (step 1750). If yes, e.g. all the tissue segments are characterized as having a clean margin then the achieving of a clean margin process is completed. If no, then tissue segments which correspond and/or are adjacent to the location of the tissue segments at which there was no clean margin are removed (step 1755), for example using a scalpel, or a diathermal knife. The removed tissue segments and/or the surface of the tissue from where the tissue was removed are characterized (step 1760), and their margin status is recorded (step 1770). Then, the clean margin process returns to the first step 1750 of the control cycle for determining whether the removed tissue and/or the surface of the tissue from where the tissue segments were removed are characterized as clean margin. The clean margin process is continued in the control cycle until the margin status of all the characterized tissue segments is clean.

Figure 17:
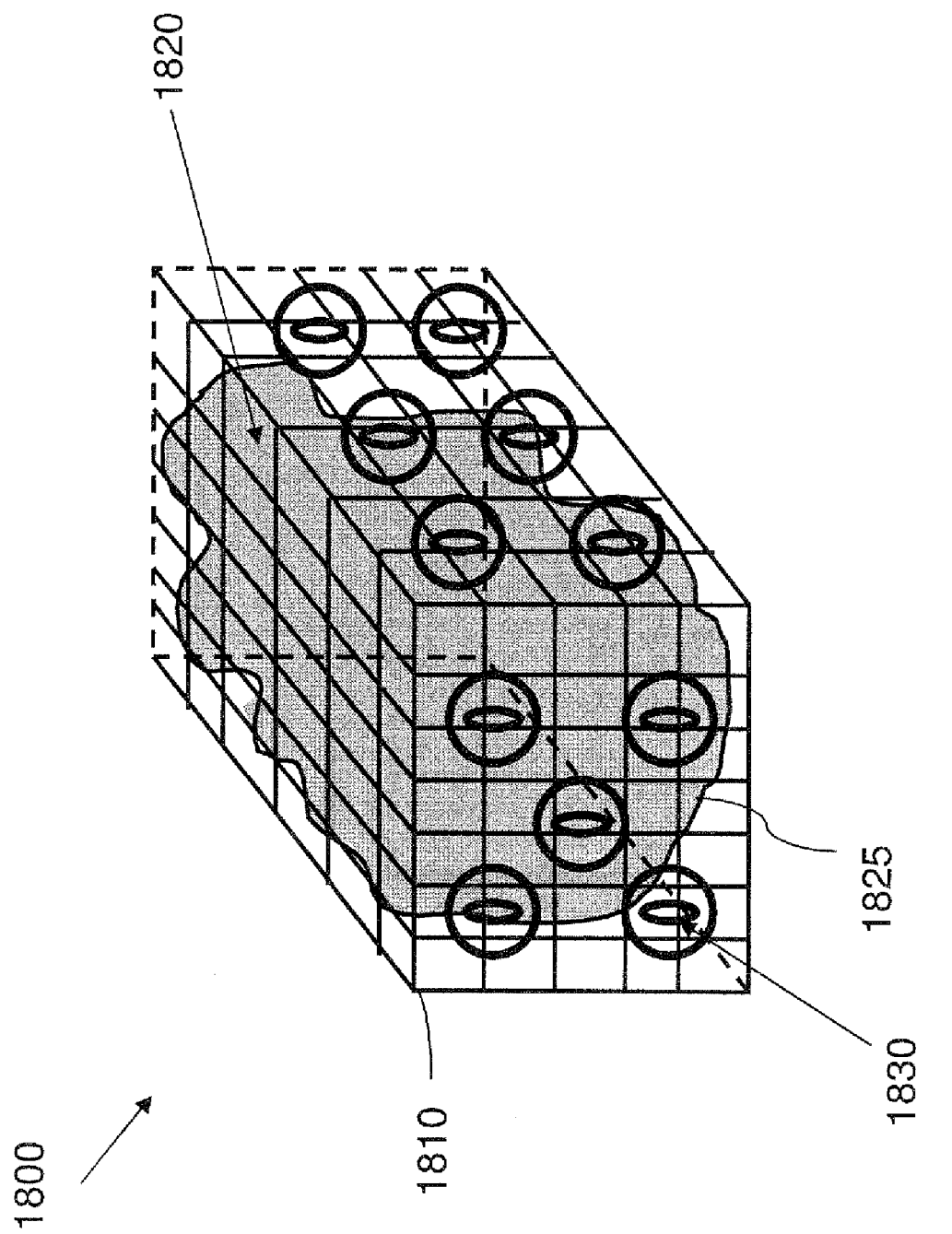
FIG. 17 exemplifies a device of the present invention for holding and characterizing a tissue or an anatomical feature during a clean-margin assessment process.

Reference is now made to FIG. 17 illustrating a device 1800 for holding and characterizing a tissue or an anatomical feature, for example during a clean-margin assessment process, in accordance with some embodiments of the present invention. The device 1800 includes a body or housing 1810, configured for receiving and holding a tissue or the tissue portion (e.g. as shown in FIGS. 15a-15c), or a body lumen portion, a skin portion or an anatomical feature. According to one embodiment of the present invention, one or more sensors such as tissue-type sensors 1830, or an array of sensors such as a rectangular array or matrix of optical sensor elements, may be attached or mounted on the housing 1810 for sensing and characterizing the tissue surface 1825, for example of an anatomical structure 1820, to indicate a clean margin.

The housing 1810 may be shaped to conform to the surface of the anatomical feature 1820. Therefore, the anatomical feature 1820 may be sensed or scanned from any direction, without being limited by the shape of the housing 1810. According to one embodiment of the present invention, the sensors or the array of sensors may be attached to the inner side of the housing 1810 for sensing or scanning for example an anatomical structure which is enclosed by the housing. According to another embodiment of the present invention, the sensors or the array of sensors may be attached to the outer side or surface of the housing 1810 for sensing or scanning for example an anatomical structure which surrounds the outer side of housing 1810. According to some embodiments of the present invention, one or more sensors such as the as tissue-type sensors 1830 may be attached to and cover the whole surface of the housing 1810, thus enabling sensing or scanning the whole surface of the anatomical structure simultaneity in real time.

The housing 1810 may be formed as a rigid body such as cube, or a sphere, or an ellipsoid. Additionally, or alternatively, the housing 1810 may be formed, for example as a flexible body such as a stretchable body, an expansible body, a sac-like mesh, a stretchable stocking, or a resilient cage.

Such housing 1810 may be similar to various embodiments described, for example, in international publication number WO 2006/092797, entitled "Device And Method For Transporting And Handling Tissue", assigned to the common assignee of the present application and incorporated herein by reference.

According to some embodiments of the present invention, a tissue surface, such as the tissue surface 1825, may be scanned or sensed by using a relative displacement between the housing and/or the sensors, e.g. by rotating the sensors 1830 or an array of sensors and/or the housing 1810, using for example a robotic arm or a motor. For example, one or more sensors 1830 may be connected to a robotic arm which is configured to move and rotate the sensors 1830 and scan the tissue surface 1825 of the anatomical feature 1820 to indicate the margin status at the anatomical feature 1825, while the housing 1810 holds the anatomical feature 1820. According to some other embodiments of the present invention, the housing 1810 may be rotated as it holds the anatomical feature 1820 and the sensors 1830 or the array of sensors may sense and/or scan the anatomical feature 1820 to indicate the margin status at the anatomical feature 1825, while the sensors or the array of sensors are stable and fixed.

The tissue surface 1825 may include a specific positional reference with respect to the body from which it was taken, or is being taken, and the device 1800 is designed to maintain the tissue positional reference, by providing, for example a rigid frame of reference for it.

The feature/tissue characterizing device 1800 may be applied to the feature/tissue after the tissue 1825 or the anatomical feature 1820 have been removed from the body, or while the tissue 1825 or the anatomical feature are being removed.

In operation, a tissue (such as the tissue 1505 or the tissue portion 1550 shown in FIGS. 15*a*-15*c*), a body lumen portion, a skin portion or an anatomical feature, such as the anatomical feature 1820 may be inserted into the device 1800, or may be attached to the outer surface of the housing 1810 for identifying whether there is a clean margin, for example at the tissue surface of the anatomical feature. The tissue or the anatomical feature 1820 is characterized, preferably in real time, by rotating the housing 1810 and/or the sensors 1830 of the device 1800 or by activating the array of sensors. Signals from the sensors 1830 are transferred for analysis to a computerized system, such as the computerized system 95 for clean-margin assessment, described hereinabove in conjunction with FIG. 6. If the anatomical feature 1820 is characterized as having a clean margin then the clean margin process is completed. If the anatomical feature does not have a clean margin then an additional anatomical feature adjacent to the anatomical feature which did not have a clean margin, or a tissue corresponding/adjacent to at least the location of the tissue at which there was no clean margin, is removed from the body as described hereinabove in conjunction with FIGS. 16*a* and 16*b*.

According to some embodiments of the present invention, the device 1800 may be constructed as a continuous surface carrying sensors, such as sensors 1830, mounted on its inner side. Such a continuous surface has an opening for connection to a vacuum source. The device 1800 may further include a mechanism for generating suction within it, for example by connecting it to a vacuum source. When suction (e.g. vacuum) is applied to the housing 1810 of device 1800, for example when a tissue portion is enclosed within the housing 1800, negative pressure present within the housing 1810 will result in the deformation of the housing so that its shape will match to the tissue within it, thereby attaching the tissue or the anatomical feature 1820 to the sensors 1830 or to the active areas thereof. Once the tissue within the housing has been attached to the sensor array active areas, a tissue characterization process is initiated.

Figure 18:
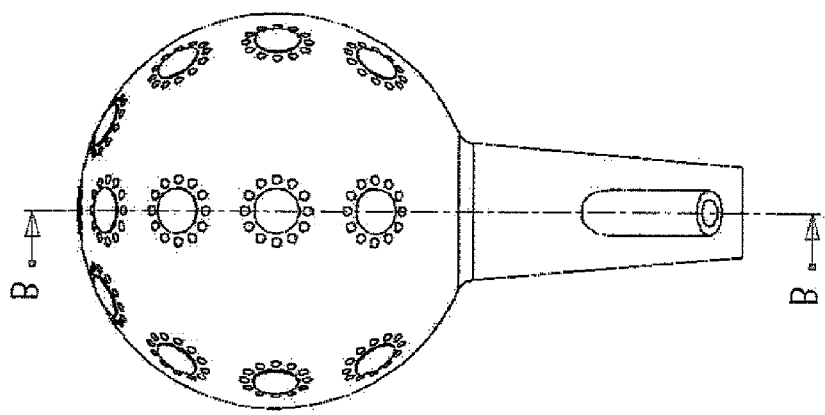
FIGS. 18a and 18b illustrate a side view and a three dimension view, respectively, of a sensor array frame structure.
Figure 18:
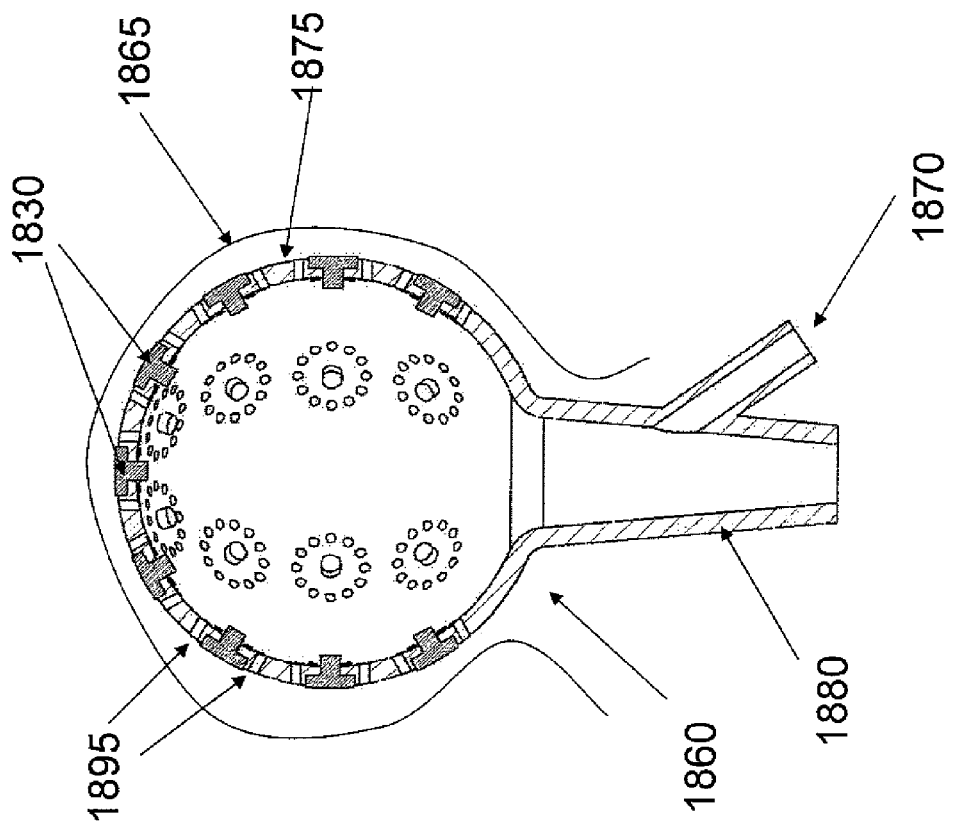

According to some embodiments of the present invention, as shown in FIG. 17 and more specifically in FIGS. 18A and 18B, one or more sensors such as sensors 1850 or 1830, e.g. array sensors, may be mounted on or attached to the outer surface of a sensor array frame structure 1860 or the device 1800 to characterize tissue, such as tissue 1865 enclosing and/or surrounding the sensor array frame structure 1860 or device 1800. The sensor array frame structure 1860 or device 1800 may be formed, for example, but not limited to, as a sphere, an ellipsoid, a tube, or a shape conforming to a body anatomical feature. The sensor array structure 1860 further includes a signal communication bundle 1870 for transmitting and receiving signals from and to the sensors 1850. The signal communication with the sensors 1850 may be performed, for example as described in co-pending US application entitled "PROBES, SYSTEMS, AND METHODS FOR EXAMINING TISSUE ACCORDING TO THE DIELECTRIC PROPERTIES THEREOF" filed on May 1, 2007 whose disclosure is incorporated herein by reference. Each of the sensors may have a dedicated signal communication line. Alternatively, a common signal communication line is employed associated with multiple sensors and operable with multiplexing, for example, time multiplexing, or wavelength multiplexing.

The tissue 1865 surrounding the sensor array structure may be in a form of a closed continuous tissue surface, for example a cavity or a closed lumen. The cavity may be either a natural body cavity, or a cavity formed by removal of tissue during a surgical procedure, for example partial mastectomy or lumpectomy breast cancer removal surgical procedures. The closed lumen may be, for example, a blocked or truncated or an artificially closed lumen.

According to some embodiments of the present invention, the sensor array structure 1860 may include a mechanism for generating suction within it, configured to enable a contact and release between the sensor array frame structure 1860 and the tissue 1865, ensuring a reliable and effective tissue-characterization.

As shown in the present example, the sensor array frame structure 1860 includes one or more connection locations (openings and possible appropriate connectors extending from said openings) 1880 for connecting a vacuum source (not shown) to the sensor array frame structure 1860, and one or more perforations (holes) 1895, arranged in a spaced-apart relationship within the surface of the structure 1860 to enable vacuum communication between the vacuum source and the outer surface 1875 of the structure 1860. When the sensor array structure 1860 is surrounded by a closed continuous tissue surface, such as tissue 1865, the holes 1895 enable vacuum communication between the vacuum source and the closed continuous tissue surface surrounding the sensor array structure.

In operation, for example during surgery, the sensor array frame structure 1860 is inserted, for example, into an opening in a closed continuous tissue surface. Following the insertion of the sensor array frame structure 1860, the opening of the closed continuous tissue surface is tightly attached around the connection location 1880, thus forming a closed continuous tissue surface with its only opening 1880 directly connected to the vacuum source. When vacuum (i.e. suction) from the vacuum source is applied to the interior of the sensor array structure, vacuum communication between the inner and outer surfaces of the sensor array structure and the closed continuous tissue surface is formed, due to the existence of holes 1895 across the structure surface. The negative pressure present at the outer surface of the sensor array structure 1860 results in the collapse of the closed continuous tissue surface 1865 and attachment of this surface onto the external surface of the sensor array structure 1860, where the sensors 1850 are located. Once the closed continuous tissue surface has attached itself to the sensor array active areas, a tissue characterization process is initiated.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A method for examining body tissue, the method comprising:
   examining a tissue portion excised from a subject's body and establishing a clean-margin of healthy tissue around an abnormal tissue within said excised tissue portion, said establishing comprising:
   characterizing a tissue segment of an exposed surface of the excised tissue portion to determine and record the tissue segment margin status;
   analyzing the tissue segment margin status and identifying whether it corresponds to clean margin or not, thereby enabling further excision, from the body, of tissue segments which are adjacent or correspond to the tissue segments which were not identified as clean margin.

2. The method of claim 1, comprising characterizing all tissue segments of said tissue surface and determining whether the tissue is identified as clean margin, thereby enabling the removal of tissues which are adjacent/correspond to any of said tissue segments which were not identified as clean margin.

3. The method according to claim 2, comprising characterizing said tissue segments in real time.

4. The method of claim 2 comprising defining clean margin status targets.

5. The method of claim 2 comprising: providing a device for characterizing the tissue, said device comprising a housing configured for holding the tissue, at least one sensor mounted on the housing and configured for characterizing the tissue; providing a mechanism configured to attach said tissue to the housing; and surrounding the device by said tissue.

6. The method of claim 5 comprising providing suction to the device from a vacuum source.

7. The method of claim 5 wherein the at least one sensor comprises an array of sensing elements.

8. The method according to claim 5 wherein the housing has a body having one of the following configurations: a rigid body, a flexible body, a stretchable body, and an expansible body.

9. The method of claim 1, wherein the abnormal tissue is cancerous tumor.

10. The method of claim 2 comprising:
    providing a device for characterizing the tissue, said device comprising a housing configured to be enclosed by said tissue, at least one sensor mounted on the housing and configured for characterizing the tissue; providing a mechanism configured to attach said tissue to the housing; and surrounding or enclosing the device by said tissue.

11. A method for use in examining a tissue, the method comprising:
    providing a tissue portion excised from a subject's body;
    examining said excised tissue portion and establishing a clean-margin of healthy tissue around an abnormal tissue within said excised tissue portion, said establishing comprising:
    providing a device for characterizing a tissue, said device comprising a housing configured to be enclosed by said tissue and having a tissue-contacting surface, and at least one tissue-type sensor mounted on the housing and configured for characterizing a type of said tissue, and
    providing a mechanism configured to attach said tissue to the housing so that the tissue-contacting surface is in contact with an exposed surface of the excised tissue portion;
    surrounding or enclosing the device by said tissue;
    characterizing all segments of a surface of said tissue;
    recording margin status of said segments;
    identifying whether said tissue segments correspond to clean margin; and
    removing in case said tissue segments include one or more segments that do not correspond to clean margin, further excising from the body only tissue segments which are adjacent or correspond to tissue segments which were not identified as clean margin until the margin status of all the characterized tissue segments in excised tissue is clean.

12. The method according to claim 11 comprising rotating the at least one sensor and scanning said surface of said tissue while the housing holds said tissue.

13. The method according to claim 11 comprising rotating the housing and scanning said surface of said tissue while the at least one sensor is fixed.

14. The method according to claim 11 comprising rotating the housing and the at least one sensor, while said at least one sensor scans said surface of said tissue.

15. The method according to claim 11 wherein said at least one sensor is connected to a robotic arm.

16. A device for characterizing an exposed tissue surface, said device comprises:
    a housing having a tissue-contacting surface configured to, when being brought in contact with the exposed tissue surface, be enclosed by a portion of the exposed tissue surface portion;
    at least one tissue-type sensor, mounted on the housing so as to extend substantially to said tissue-contacting surface to be exposed to the exposed tissue surface, said at least one tissue-type sensor being configured and operable for characterizing a tissue segment of said exposed tissue surface to determine and record the tissue segment margin status; and
    a mechanism configured to attach said tissue surface to the housing.

17. The device according to claim 16 comprising a connector to a vacuum source.

18. The device according to claim 17 wherein said housing comprises one or more openings to enable vacuum communication between said tissue and said vacuum source.

19. The device according to claim 16 comprising at least one signal communication bundle for transmitting and receiving signals from and to the at least one sensor.

20. The device according to claim 16 configured to be surrounded by a closed continuous tissue surface.

21. The device according to claim 16 wherein the housing is configured to be surrounded or enclosed by the tissue in the form of a cavity or a closed lumen.

22. The device according to claim 16 comprising a robotic arm for rotating said at least one sensor with respect to the housing.

23. The device according to claim 16 comprising a robotic arm for rotating the housing with respect to said at least one sensor.

24. The device according to claim 16 wherein the housing has a body having one of the following configurations: a rigid body, a flexible body, a stretchable body, and an expansible body.

25. The device according to claim 16 wherein the sensor is attached to either the inner or the outer side of the housing.

26. The method of claim 16 wherein the sensor comprises an array of sensing elements.

27. A device for holding a tissue surface in a tissue characterization procedure, the device comprising:

a housing having a tissue-contacting surface and a sensor array frame structure carrying one or more tissue-type sensors, and a plurality of holes on said tissue contacting surface of said housing, said holes being arranged in groups of at least three holes/group, each group surrounding one of said one or more sensors; and a channel of fluid communication between said holes and a vacuum source.

28. A device according to claim 27, comprising a signal communication bundle for transmitting and receiving signals from and to the sensors.

* * * * *